US010822325B2

(12) United States Patent
Oprea et al.

(10) Patent No.: US 10,822,325 B2
(45) Date of Patent: Nov. 3, 2020

(54) HUMAN GLUT5 SPECIFIC INHIBITORS AND METHODS OF TREATMENT

(71) Applicants: UNM RAINFOREST INNOVATIONS, Albuquerque, NM (US); ROSALIND FRANKLIN UNIVERSITY, North Chicago, IL (US)

(72) Inventors: Tudor I. Oprea, Albuquerque, NM (US); Cristian George Bologa, Albuquerque, NM (US); Oleg Ursu, Albuquerque, NM (US); Jun-Yong Choe, Libertyville, IL (US); Cristina Iancu, Libertyville, IL (US)

( * ) Notice: Subject to any disclaimer, the term of this patent is extended or adjusted under 35 U.S.C. 154(b) by 0 days.

(21) Appl. No.: 15/735,840

(22) PCT Filed: Jun. 10, 2016

(86) PCT No.: PCT/US2016/036872
§ 371 (c)(1),
(2) Date: Dec. 12, 2017

(87) PCT Pub. No.: WO2016/201214
PCT Pub. Date: Dec. 15, 2016

(65) Prior Publication Data
US 2018/0170897 A1 Jun. 21, 2018

Related U.S. Application Data

(60) Provisional application No. 62/174,630, filed on Jun. 12, 2015.

(51) Int. Cl.
C07D 317/66 (2006.01)
A61K 31/36 (2006.01)
A61P 3/10 (2006.01)
G16B 35/00 (2019.01)
G16C 20/60 (2019.01)
C07C 317/36 (2006.01)
A23L 33/125 (2016.01)
A61K 45/06 (2006.01)

(52) U.S. Cl.
CPC .......... C07D 317/66 (2013.01); A23L 33/125 (2016.08); A61K 31/36 (2013.01); A61K 45/06 (2013.01); C07C 317/36 (2013.01); G16B 35/00 (2019.02); G16C 20/60 (2019.02); A23V 2002/00 (2013.01)

(58) Field of Classification Search
CPC .............................. C07D 317/66; A61K 31/36
See application file for complete search history.

(56) References Cited

FOREIGN PATENT DOCUMENTS

EP      0711541 A1    5/1996

OTHER PUBLICATIONS

CAS Registry No. 852702-51-3, Entered Jun. 22, 2005.*
MedicineNet.com (2004) Web<http://www.medterms.com>.*
A.M. Rouhi. Chem. & Eng. News, (2003), 81(8), 32-35.*
Morissette, Sherry. Adv. Drug Delivery Rev. 2004, 56, 275-300.*
Thompson, Alayna M.George. Scientific Reports (2016) 6:24240 1-9.*
Vos MB, et al. Dietary fructose consumption among US children and adults: the Third National Health and Nutrition Examination Survey. Medscape J. Med. 10, 160 (2008).
Tappy, L. & Le, K.-A. Metabolic effects of fructose and the worldwide increase in obesity. Physiol. Rev. 90, 23-46 (2010).
Hwang IS. et al. Fructose-induced insulin resistance and hypertension in rats. Hypertension 10, 512-516 (1987).
Burant, C. F., et al. Fructose transporter in human spermatozoa and small intestine is GLUT5. J. Biol. Chem. 267, 14523-14526 (1992).
Thorens, B. & Mueckler, M. Glucose transporters in the 21st Century. Am. J. Physiol. Endocrinol. Metab. 298, E141-145 (2010).
Uldry, M. & Thorens, B. The SLC2 family of facilitated hexose and polyol transporters. Pflüg. Arch. Eur. J. Physiol. 447, 480-489 (2004).
Douard V, Ferraris, RP. Regulation of the fructose transporter GLUT5 in health and disease. Am. J. Physiol.—Endocrinol. Metab. 295, E227-E237 (2008).
David ES, et al. Dietary Induction of Intestinal Fructose Absorption in Weaning Rats. Pediatr. Res. 37, 777-782 (1995).
Stuart, CA; et al. Overexpression of GLUT5 in Diabetic Muscle Is Reversed by Pioglitazone. Diabetes Care 30, 925-931 (2007).
Mate, A; et al. Regulation of D-Fructose Transporter GLUT5 in the Ileum of Spontaneously Hypertensive Rats. J. Membr. Biol. 199, 173-179 (2004).
Godoy, A. et al. Differential subcellular distribution of glucose transporters GLUT1-6 and GLUT9 in human cancer: Ultrastructural localization of GLUT1 and GLUT5 in breast tumor tissues. J. Cell. Physiol. 207, 614-627 (2006).
Zamora-Leon S. P. et al. Expression of the fructose transporter GLUT5 in human breast cancer. Proc. Natl. Acad. Sci. U. S. A. 93, 1847-1852 (1996).
Gaster M, et al. GLUT4 Is Reduced in Slow Muscle Fibers of Type 2 Diabetic Patients Is Insulin Resistance in Type 2 Diabetes a Slow, Type 1 Fiber Disease? Diabetes 50, 1324-1329 (2001).
Deng, D. et al. Crystal structure of the human glucose transporter GLUT1. Nature 510, 121-125 (2014).

(Continued)

Primary Examiner — Mark L Shibuya
Assistant Examiner — Laura M Daniel
(74) Attorney, Agent, or Firm — Henry D. Coleman; R. Neil Sudol

(57) ABSTRACT

The present invention relates to compounds which have been discovered to be potent ligands (inhibitors) of human GLUT5 (glucose transporter type 5), a facilitative glucose transporter that transports fructose, and their use as ligands assays which can uncover additional ligands of GLUT5, having the potential for being used as drugs. In addition, the present invention is directed to compounds, chemical compositions and methods for treating disease states and conditions which are mediated through GLUT5, including such disease states and conditions as GLUT5 deficiency syndrome, diabetes (type I and II), cancer, metabolic diseases including metabolic syndrome and fatty liver disease, among others.

17 Claims, 21 Drawing Sheets

(56) References Cited

OTHER PUBLICATIONS

Sun, L. et al. Crystal structure of a bacterial homologue of glucose transporters GLUT1-4. Nature 490, 361-366 (2012).

Iancu CV, et al. Crystal structure of a glucose/H+ symporter and its mechanism of action. Proc. Natl. Acad. Sci. U. S. A. 110, 17862-17867 (2013).

Emsley, P; et al. Features and development of Coot. Acta Crystallogr. D Biol. Crystallogr. 66, 486-501 (2010).

Krissinel E. & Henrick, K. Secondary-structure matching (SSM), a new tool for fast protein structure alignment in three dimensions. Acta Crystallogr. D Biol. Crystallogr. 60, 2256-2268 (2004).

Hruz P. W. & Mueckler, M. M. Cysteine-scanning mutagenesis of transmembrane segment 7 of the GLUT1 glucose transporter. J. Biol. Chem. 274, 36176-36180 (1999).

Corpe, C. P. et al. The regulation of GLUT5 and GLUT2 activity in the adaptation of intestinal brush-border fructose transport in diabetes. Pflüg. Arch. Eur. J. Physiol. 432, 192-201 (1996).

Kasahara, T. & Kasahara, M. Expression of the rat GLUT1 glucose transporter in the yeast Saccharomyces cerevisiae. Biochem. J. 315 (Pt 1), 177-182 (1996).

Davidson, N. O. et al. Human intestinal glucose transporter expression and localization of GLUT5. Am. J. Physiol. 262, C795-800 (1992).

Young, S. M. et al. Duplex high-throughput flow cytometry screen identifies two novel formylpeptide receptor family probes. Cytom. Part J. Int. Soc. Anal. Cytol. 75, 253-263 (2009).

Bologa, C. G. et al. Virtual and biomolecular screening converge on a selective agonist for GPR30. Nat. Chem. Biol. 2, 207-212 (2006).

Dennis, M. K. et al. In vivo effects of a GPR30 antagonist. Nat. Chem. Biol. 5, 421-427 (2009).

Strouse, J. J. et al. A selective ATP-binding cassette subfamily G member 2 efflux inhibitor revealed via high-throughput flow cytometry. J. Biomol. Screen. 18, 26-38 (2013).

Williamson, E. A. et al. Targeting the transposase domain of the DNA repair component Metnase to enhance chemotherapy. Cancer Res. 72, 6200-6208 (2012).

Bologa, C. G. & Oprea, T. I. Compound collection preparation for virtual screening. Methods Mol. Biol. Clifton NJ 910, 125-143 (2012).

Mueckler, M. & Makepeace, C. Ligand-induced movements of inner transmembrane helices of Glut1 revealed by chemical cross-linking of di-cysteine mutants. PloS One 7, e31412 (2012).

Salas-Burgos A, et al. Predicting the three-dimensional structure of the human facilitative glucose transporter glut1 by a novel evolutionary homology strategy: insights on the molecular mechanism of substrate migration, and binding sites for glucose and inhibitory molecules. Biophys. J. 87, 2990-2999 (2004).

McGann M. Fred pose prediction and virtual screening accuracy. J. Chem. Inf. Model. 51, 578-596 (2011).

Rogers, D. & Hahn, M. Extended-Connectivity Fingerprints. J. Chem. Inf. Model. 50, 742-754 (2010).

Hawkins, PCD, et al. Conformer Generation with OMEGA: Algorithm and Validation Using High Quality Structures from the Protein Databank and Cambridge Structural Database. J. Chem. Inf. Model. 50, 572-584 (2010).

Halgren, T. A. Merck molecular force field. I. Basis, form, scope, parameterization, and performance of MMFF94. J. Comput. Chem. 17, 490-519 (1996).

Harkins PCD, et al. Comparison of shape-matching and docking as virtual screening tools. J. Med. Chem. 50, 74-82 (2007).

McQuade DT, et al. Passive fructose transporters in disease: a molecular overview of their structural specificity. Org. Biomol. Chem. 11, 4909-4920 (2013).

Braman J, et al. Site-directed mutagenesis using double-stranded plasmid DNA templates. Methods Mol. Biol. Clifton NJ 57, 31-44 (1996).

Geertsma, ER; et al. Membrane reconstitution of ABC transporters and assays of translocator function. Nat. Protoc. 3, 256-266 (2008).

Kaback H. R. Bacterial membranes. Methods Enzymol. 22, 99-120 (1971).

Short, SA; et al. Localization of D-lactate dehydrogenase in native and reconstituted Escherichia coli membrane vesicles. J. Biol. Chem. 250, 4291-4296 (1975).

Kraulis P. J. MOLSCRIPT: a program to produce both detailed and schematic plots of protein structures. J. Appl. Crystallogr. 24, 946-950 (1991).

Merritt, E. A. & Bacon, D. J. Raster3D: photorealistic molecular graphics. Methods Enzymol. 277, 505-524 (1997).

Larkin, M. A. et al. Clustal W and Clustal X version 2.0. Bioinforma, Oxf. Engl. 23, 2947-2948 (2007).

Database CA [online] RN 852702-51-3, Jun. 22, 2005; Retrieved from STN.

Database CA [online] RN 1241653-93-9, Sep. 16, 2010; Retrieved from STN.

Database CA [online] RN 897293-62-8, Jul. 28, 2006; Retrieved from STN.

Database CA [online] RN 1062023-52-2, Oct. 16, 2008; Retrieved from STN.

Database CA [online] RN 1111583-24-2, Feb. 25, 2009; Retrieved from STN.

Database CA [online] RN 877837-54-2, Mar. 23, 2007; Retrieved from STN.

Database CA [online] RN 879413-93-1; Retrieved from STN, Jun. 4, 2016.

Database CA [online] RN 1153116-99-4, Jul. 6, 2009; Retrieved from STN.

Database CA [online] RN 1305391-49-4; Retrieved from STN, May 6, 2011.

Database CA [online] RN 1304195-99-0, Feb. 6, 2011; Retrieved from STN.

Database CA [online] RN 1286511-46-3, Apr. 27, 2011; Retrieved from STN.

Database CA [online] RN 1153121-76-6, Jul. 6, 2009; Retrieved from STN.

Database CA [online] RN 930742-27-1, Apr. 18, 2007; Retrieved from STN.

Database CA [online] RN 1031112-97-6, Jun. 27, 2008; Retrieved from STN.

* cited by examiner

FIG. 1

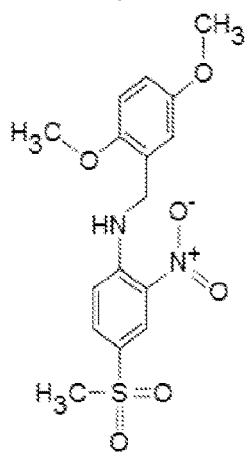

Preferred IUPAC Name = N-[(2,5-dimethoxyphenyl)methyl]-4-methanesulfonyl-2-nitroaniline

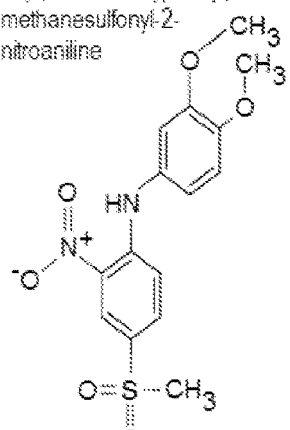

Preferred IUPAC Name = N-(3,4-dimethoxyphenyl)-4-methanesulfonyl-2-nitroaniline

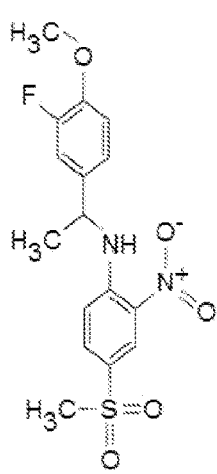

Preferred IUPAC Name = N-[1-(3-fluoro-4-methoxyphenyl)ethyl]-4-methanesulfonyl-2-nitroaniline

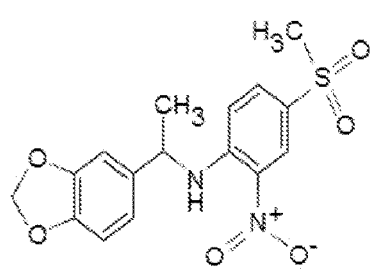

Preferred IUPAC Name = N-[1-(2H-1,3-benzodioxol-5-yl)ethyl]-4-methanesulfonyl-2-nitroaniline

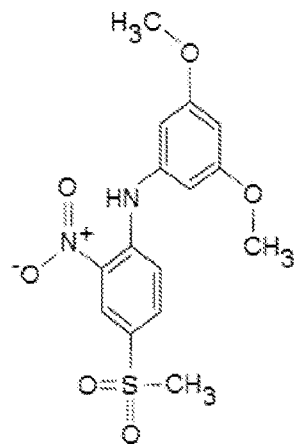

Preferred IUPAC Name = N-(3,5-dimethoxyphenyl)-4-methanesulfonyl-2-nitroaniline

FIG. 4
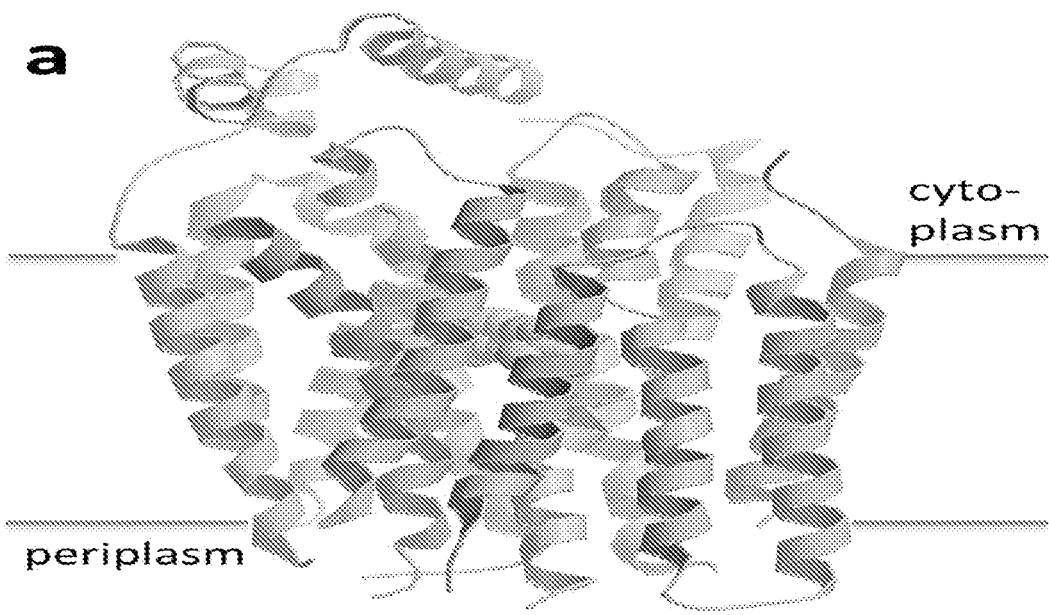
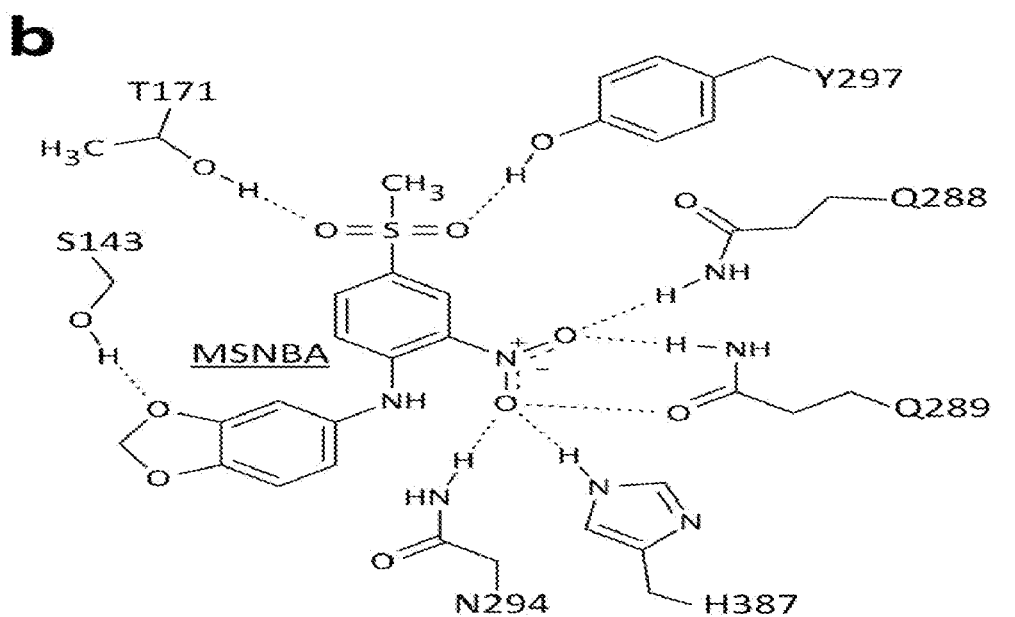
c
| | H4 | H5 | H7 | | | | H10 |
|---|---|---|---|---|---|---|---|
| GlcP$_{Se}$ | M$_{113}$ | T$_{141}$ | Q$_{250}$ | Q$_{251}$ | N$_{256}$ | I$_{259}$ | F$_{348}$ |
| GLUT1 | T$_{137}$ | V$_{165}$ | Q$_{282}$ | Q$_{283}$ | N$_{288}$ | F$_{291}$ | F$_{379}$ |
| GLUT2 | S$_{169}$ | V$_{197}$ | Q$_{314}$ | Q$_{315}$ | N$_{320}$ | F$_{323}$ | F$_{411}$ |
| GLUT3 | T$_{135}$ | V$_{163}$ | Q$_{280}$ | Q$_{281}$ | N$_{286}$ | F$_{289}$ | F$_{377}$ |
| GLUT4 | S$_{153}$ | V$_{181}$ | Q$_{298}$ | Q$_{299}$ | N$_{304}$ | F$_{307}$ | F$_{395}$ |
| GLUT5 | S$_{143}$ | T$_{171}$ | Q$_{288}$ | Q$_{289}$ | N$_{294}$ | Y$_{297}$ | H$_{387}$ |

FIG. 9
Table 1 | Compounds tested for GLUT5 transport inhibition.
MSNBA is highlighted in bold italics, and related inhibitory compounds are in italics.

| SMILES | Supplier | MW | CHEM_NAME |
|---|---|---|---|
| [N+](=O)([O-])c1c(ccc(c1)C)NC2OC(C(C2O)O)CO | ChemBridge | 284.27 | N-(4-methyl-2-nitrophenyl)pentofuranosylamine |
| [N+](=O)([O-])c1c(cccc1)NC2OC(C(C2O)O)CO | ChemBridge | 270.24 | N-(2-nitrophenyl)pentofuranosylamine |
| [N+](=O)([O-])c1c(ccc(c1)C#N)NCc2cc(c(cc2)O)O | Enamine | 285.26 | 4-[(3,4-dihydroxybenzyl)amino]-3-nitrobenzonitrile |
| [N+](=O)([O-])c1c(ccc(c1)[N+](=O)[O-])NCCCCO | ChemDiv | 255.23 | 4-(2,4-dinitroanilino)-1-butanol |
| N(CC2OC(C(C2O)O)CO)c1ccc(cc1)C | Labotest | 253.3 | 2,5-anhydro-1-deoxy-1-(4-toluidino)hexitol |
| *[S](=O)(=O)(C)c1cc(c(cc1)NCc2c(ccc(c2)OC)OC)[N+](=O)[O-]* | *Enamine* | *366.39* | *N-(2,5-dimethoxybenzyl)-N-[4-(methylsulfonyl)-2-nitrophenyl]amine* |
| [S](=O)(=O)(C)c1cc(c(cc1)NCC2OCCC2)[N+](=O)[O-] | Enamine | 300.34 | 4-(methylsulfonyl)-2-nitro-N-(tetrahydro-2-furanylmethyl)aniline |
| [N+](=O)([O-])c1c(ccc(c1)[N+](=O)[O-])NCCNCCO | Vitas-M | 270.24 | 2-{[2-(2,4-dinitroanilino)ethyl]amino}ethanol |
| [N+](=O)([O-])c1ccc(cc1)NC2OC(C(C2O)O)CO | ChemBridge | 270.24 | N-(4-nitrophenyl)pentofuranosylamine |
| Clc1c(ccc(c1)[N+](=O)[O-])NCc2cc(c(cc2)OC)O | Enamine | 308.72 | 5-[(2-chloro-4-nitroanilino)methyl]-2-methoxyphenol |
| [n]2(ncnc2)C1OC(C(C1O)O)CO | AMS Private | 201.18 | 2-(hydroxymethyl)-5-(1H-1,2,4-triazol-5-yl)tetrahydrofuran-3,4-diol |
| [S](=O)(=O)(C)c1cc(c(cc1)NCCc2nc(n[o]2)N)[N+](=O)[O-] | Enamine | 327.32 | N-[2-(3-amino-1,2,4-oxadiazol-5-yl)ethyl]-N-[4-(methylsulfonyl)-2-nitrophenyl]amine |
| [N+](=O)([O-])c1cc(c(cc1)NCc2ccc(cc2)N)C(=O)OC | Key Organics / BIONET | 301.3 | methyl 2-[(4-aminobenzyl)amino]-5-nitrobenzoate |
| [N+](=O)([O-])c1c(ccc(c1)C(=O)C)NCc2cc(c(c(c2)C)O)C | Enamine | 314.34 | 1-{4-[(4-hydroxy-3,5-dimethylbenzyl)amino]-3-nitrophenyl}ethanone |

FIG. 9 (cont.)

| SMILES | Supplier | MW | CHEM_NAME |
|---|---|---|---|
| [N+](=O)([O-])c1cc(c(cc1)NCc2[o]ccc2)C(=O)O | Maybridge Ltd | 262.22 | 2-[(2-furylmethyl)amino]-5-nitrobenzoic acid |
| [N+](=O)([O-])c1cc(ccc1)C(=O)NCc2c(nc(cc2C)C)O | Enamine | 315.33 | 1-(4-{[(2-hydroxy-4,6-dimethyl-3-pyridinyl)methyl]amino}-3-nitrophenyl)ethanone |
| [N+](=O)([O-])c1cc(c(cc1)NCC2C(CCC2)O)C(=O)NC | Enamine | 293.32 | 2-{[(2-hydroxycyclopentyl)methyl]amino}-N-methyl-5-nitrobenzamide |
| [S](=O)(=O)(C)c1cc(c(cc1)NCc2[o]ccc2)[N+](=O)[O-] | Enamine | 296.3 | N-(2-furylmethyl)-4-(methylsulfonyl)-2-nitroaniline |
| [S](=O)(=O)(N)c1cc(c(cc1)NCC2OCCC2)[N+](=O)[O-] | Enamine | 301.32 | 3-nitro-4-[(tetrahydro-2-furanylmethyl)amino]benzenesulfonamide |
| [N+](=O)([O-])c1c(ccc(c1)C(=O)C)NCc2c(ccc(c2)OC)O C | Enamine | 330.34 | 1-{4-[(2,5-dimethoxybenzyl)amino]-3-nitrophenyl}ethanone |
| [S](=O)(=O)(N)c1cc(c(cc1)NCCc2c([nH]nc 2O)C)[N+](=O)[O-] | Enamine | 341.35 | 4-{[2-(3-hydroxy-5-methyl-1H-pyrazol-4-yl)ethyl]amino}-3-nitrobenzenesulfonamide |
| [N+](=O)([O-])c1c(ccc(c1)C(=O)O)NC(C)c2ncccc2 | Enamine | 287.27 | 3-nitro-4-{[1-(2-pyridinyl)ethyl]amino}benzoic acid |
| S([C@H]2OC(C(C2O)O)[C@@H](O)CO)c 1ccccc1 | Sigma-Aldrich | 272.32 | phenyl 1-thio-beta-L-erythro-hexofuranoside |
| Fc1c(ccc(c1)[N+](=O)[O-])NCc2cc(c(cc2)O)OC | Enamine | 292.27 | 4-[(2-fluoro-4-nitroanilino)methyl]-2-methoxyphenol |
| [s]1c(nc(c1)CNc2cc(cc(c2)C(=O)C)[N+](=O)[O-])NC | Enamine | 306.35 | 1-[4-({[2-(methylamino)-1,3-thiazol-4-yl]methyl}amino)-3-nitrophenyl]ethanone |
| [N+](=O)([O-])c1c(ccc(c1)C(=O)C)Nc2cc(c(cc2)OC)O | Enamine | 302.29 | 1-[4-(3-hydroxy-4-methoxyanilino)-3-nitrophenyl]ethanone |
| [N+](=O)([O-])c1c(ccc(c1)C(=O)O)NCc2ccccc2 | ChemDiv | 272.26 | 4-(benzylamino)-3-nitrobenzoic acid |
| [N+](=O)([O-])c1c(ccc(c1)c3n[o]c(n3)C)NCC2OCCC2 | Vitas-M | 304.31 | N-[4-(5-methyl-1,2,4-oxadiazol-3-yl)-2-nitrophenyl]-N-(tetrahydro-2-furanylmethyl)amine |
| [N+](=O)([O-])c1cc(c(cc1)NCc2c(nc(cc2C)C)O)COC | Enamine | 317.34 | |

FIG. 9 (cont.)

| SMILES | Supplier | MW | CHEM_NAME |
|---|---|---|---|
| [Na+].[S](=O)(=O)([O-])CCNc1c(cc(cc1)[N+](=O)[O-])[N+](=O)[O-] | Sigma-Aldrich | 313.22 | sodium 2-(2,4-dinitroanilino)ethanesulfonate |
| [N+](=O)([O-])c1cc(c(cc1)NCc2nc[o]c2C)C(=O)OC | Enamine | 291.26 | |
| [S](=O)(=O)(c1ccc(cc1)Nc2cc(c(cc2)O)OC)[N+](=O)[O-] | Enamine | 352.37 | N-(3,4-dimethoxyphenyl)-4-(methylsulfonyl)-2-nitroaniline |
| Clc1cc(c(cc1)NC2OC(C(C(C2O)O)O)C)[N+](=O)[O-] | ChemBridge | 318.71 | N-(4-chloro-2-nitrophenyl)-6-deoxyhexopyranosylamine |
| [N+](=O)([O-])c1cc(c(cc1)NCc2c(ccc2)OC)O)OC | Sigma-Aldrich | 304.3 | 2-methoxy-6-[(2-methoxy-4-nitroanilino)methyl]phenol |
| O1C(C(C(C1CO)O)O)OC(=O)c2ccccc2 | Sigma-Aldrich | 254.24 | 1-O-benzoyl-D-ribofuranose |
| [N+](=O)([O-])c1c(ccc1)C(=O)CNC2CCC(CC2)O | Enamine | 278.31 | 1-{4-[(4-hydroxycyclohexyl)amino]-3-nitrophenyl}ethanone |
| FC(F)(F)c1cc(cc1)NCc2cc(c(cc2)OC)OC)[N+](=O)[O-] | ChemBridge | 356.3 | N-(3,4-dimethoxybenzyl)-2-nitro-4-(trifluoromethyl)aniline |
| [N+](=O)([O-])c1c(ccc1)C(=O)NCC(CO)Cc2[o]ccc2 | Enamine | 318.33 | 1-(4-{[3-(2-furyl)-2-(hydroxymethyl)propyl]amino}-3-nitrophenyl)ethanone |
| [S](=O)(=O)(C)c1cc(c(cc1)NCc2cc(ncc2)OC)[N+](=O)[O-] | Enamine | 337.36 | N-[(2-methoxy-4-pyridinyl)methyl]-N-[4-(methylsulfonyl)-2-nitrophenyl]amine |
| [S](=O)(=O)(N)c1cc(c(cc1)NCC(=O)N2CCC(CC2)O)[N+](=O)[O-] | Enamine | 358.38 | 4-[2-(4-hydroxy-1-piperidinyl)-2-oxoethyl]amino]-3-nitrobenzenesulfonamide |
| FC(F)(F)c1c(cc(c(c1)[N+](=O)[O-])NCc2nc(c(cc2)C(O)C)Cl | Enamine | 389.76 | |
| Fc1ccc(c1)C(Nc2cc(c(cc2)[S](=O)(=O)C)[N+](=O)[O-])OC | Enamine | 368.39 | N-[1-(3-fluoro-4-methoxyphenyl)ethyl]-4-(methylsulfonyl)-2-nitroaniline |
| FC(F)(F)C(O)CCNc1c(cc(cc1)[N+](=O)[O-])C(=O)OC | Enamine | 322.24 | methyl 5-nitro-2-[(4,4,4-trifluoro-3-hydroxybutyl)amino]benzoate |
| [S](=O)(=O)(C)c1c(ccc(c1)[S](=O)(=O)C)NCCOCCO | Enamine | 337.42 | 2-{2-[2,4-bis(methylsulfonyl)anilino]ethoxy}ethanol |

FIG. 9 (cont.)

| SMILES | Supplier | MW | CHEM_NAME |
|---|---|---|---|
| [N+](=O)([O-])c1c(ccc(c1)C(=O)N)NCc2c(ccc2)OC | Enamine | 301.3 | 4-[(2-methoxybenzyl)amino]-3-nitrobenzamide |
| [N+](=O)([O-])c1c(ccc(c1)OC)NC(=O)N2CC(CCC2)O | Sigma-Aldrich | 295.3 | 3-hydroxy-N-(4-methoxy-2-nitrophenyl)-1-piperidinecarboxamide |
| [S](=O)(=O)(NC)c1cc(c(cc1)NC2CCC(CC2)O)[N+](=O)[O-] | Enamine | 329.38 | 4-[(4-hydroxycyclohexyl)amino]-N-methyl-3-nitrobenzenesulfonamide |
| [S](=O)(=O)©c1cc(c(cc1)NCCc2ncccc2)[N+](=O)[O-] | Enamine | 321.36 | 4-(methylsulfonyl)-2-nitro-N-[2-(2-pyridinyl)ethyl]aniline |
| [N+](=O)([O-])c1c(ccc(c1)[N+](=O)[O-])NCCCCCC(=O)O | Sigma-Aldrich | 297.27 | 6-(2,4-dinitroanilino)hexanoic acid |
| FC(F)[S](=O)(=O)c1cc(c(cc1)NCc2n[o]c(c2)C)[N+](=O)[O-] | Enamine | 347.3 | 4-[(difluoromethyl)sulfonyl]-N-[(5-methyl-3-isoxazolyl)methyl]-2-nitroaniline |
| [S](=O)(=O)(N)c1cc(c(cc1)NCC2Oc3c(ccc3)OC2)[N+](=O)[O-] | Enamine | 365.37 | 4-[(2,3-dihydro-1,4-benzodioxin-2-ylmethyl)amino]-3-nitrobenzenesulfonamide |
| [N+](=O)([O-])c1c(ccc(c1)C(=O)C)NCC2CN(CC2)C | Enamine | 277.32 | 1-(4-[(1-methyl-3-pyrrolidinyl)methyl]amino]-3-nitrophenyl)ethanone |
| [N+](=O)([O-])c1c(ccc(c1)[N+](=O)[O-])NCCC(=O)O | Sigma-Aldrich | 255.19 | 3-(2,4-dinitroanilino)propanoic acid |
| [N+](=O)([O-])c1cc(c(cc1)NCCc2[nH]nc(c2)O)C(=O)OC | Enamine | 306.28 | 7-[[2-(3-hydroxyphenyl)ethyl]amino]-6-nitro-4-quinazolinol |
| [N+](=O)([O-])c1cc2c(ncnc2O)cc1NCCc3cc(ccc3)O | Enamine | 326.31 | |
| [N+](=O)([O-])c1c(ccc(c1)C(=O)O)Nc2cccc(cc2)OC | ChemDiv | 288.26 | 4-(4-methoxyanilino)-3-nitrobenzoic acid |
| [N+](=O)([O-])c1c(ccc(c1)C(=O)N)NCC(CO)Cc2[o]ccc2 | Enamine | 319.32 | 4-[[3-(2-furyl)-2-(hydroxymethyl)propyl]amino]-3-nitrobenzamide |
| FC(F)[S](=O)(=O)c1cc(c(cc1)NCc2nc[s]c2)[N+](=O)[O-] | Enamine | 349.34 | 4-[(difluoromethyl)sulfonyl]-2-nitro-N-(1,3-thiazol-4-ylmethyl)aniline |

FIG. 9 (cont.)

| SMILES | Supplier | MW | CHEM_NAME |
|---|---|---|---|
| [N+](=O)([O-])c1cc(c(cc1)NCC2OCCOC2)C(=O)OC | Enamine | 296.28 | methyl 2-[(1,4-dioxan-2-ylmethyl)amino]-5-nitrobenzoate |
| [N+](=O)([O-])c1cc(c(cc1)NC2CCC(CC2)O)C(=O)OC | Enamine | 294.31 | methyl 2-[(4-hydroxycyclohexyl)amino]-5-nitrobenzoate |
| [S](=O)(=O)(C)c1cc(c(cc1)Nc2cnc(cc2)N3CCCC3)[N+](=O)[O-] | Enamine | 362.41 | N-[4-(methylsulfonyl)-2-nitrophenyl]-6-(1-pyrrolidinyl)-3-pyridinamine |
| [N+](=O)([O-])c1cc(c(cc1)NCc2c(ccc(c2)OC)OC)C | Vitas-M | 302.33 | N-(2,5-dimethoxybenzyl)-2-methyl-4-nitroaniline |
| [N+](=O)([O-])c1c(ccc(c1)C#N)NCc2c(ccc(c2)OC)OC | Enamine | 313.31 | 4-[(2,5-dimethoxybenzyl)amino]-3-nitrobenzonitrile |
| [S](=O)(=O)(NC)c1cc(c(cc1)NCC2(CCC2)O)[N+](=O)[O-] | Enamine | 315.35 | 4-{[(1-hydroxycyclobutyl)methyl]amino}-N-methyl-3-nitrobenzenesulfonamide |
| [N+](=O)([O-])c1ccc(c1)C(=O)C)NC(C)c2ncccc2 | Enamine | 285.3 | 1-(3-nitro-4-{[1-(2-pyridinyl)ethyl]amino}phenyl)ethanone |
| [N+](=O)([O-])c1cc2c(ncnc2O)cc1NCC3OCCC3 | Enamine | 290.28 | 6-nitro-7-[(tetrahydro-2-furanylmethyl)amino]-4-quinazolinol |
| [N+](=O)([O-])c1c(ccc(c1)C(=O)OC)NC(C)c2ncccc2 | Enamine | 301.3 | methyl 3-nitro-4-{[1-(2-pyridinyl)ethyl]amino}benzoate |
| FC(F)[S](=O)(=O)c1cc(c(cc1)NCc2n[nH]c(n2)C)[N+](=O)[O-] | Enamine | 347.3 | 4-[(difluoromethyl)sulfonyl]-N-[(5-methyl-1H-1,2,4-triazol-3-yl)methyl]-2-nitroaniline |
| [S](=O)(=O)(C)c1cc(c(cc1)NCC2CN(CC2)CCOC)[N+](=O)[O-] | Enamine | 357.43 | N-{[1-(2-methoxyethyl)-3-pyrrolidinyl]methyl}-N-[4-(methylsulfonyl)-2-nitrophenyl]amine |
| [N+](=O)([O-])c1c(ccc(c1)C(=O)O)NCCc2c3c([nH]c2)ccc3 | Vitas-M | 325.32 | 4-{[2-(1H-indol-3-yl)ethyl]amino}-3-nitrobenzoic acid |
| [N+](=O)([O-])c1c(ccc(c1)C(=O)O)NCCc2cc(c(cc2)O)O | Vitas-M | 318.29 | 4-(3,4-dihydroxyphenethylamino)-3-nitrobenzoic acid |
| [S](=O)(=O)(O)c1c(ccc(c1)[N+](=O)[O-])Nc2ccc(cc2)N | ChemBridge | 309.3 | 2-(4-aminoanilino)-5-nitrobenzenesulfonic acid |

FIG. 9 (cont.)

| SMILES | Supplier | MW | CHEM_NAME |
|---|---|---|---|
| [N+](=O)([O-])c1cc(c(cc1)NCC2OCCC2)C#N | Enamine | 247.25 | 5-nitro-2-[(tetrahydro-2-furanylmethyl)amino]benzonitrile |
| [N+](=O)([O-])c1c(ccc(c1)[N+](=O)[O-])NCCCN©C | Vitas-M | 304.73 | N~1~-(2,4-dinitrophenyl)-N~3~,N~3~-dimethyl-1,3-propanediamine |
| [S](=O)(=O)c1cc(c(cc1)NCC2(CC(CCC2)C)O)[N+](=O)[O-] | Enamine | 342.42 | 3-methyl-1-{[4-(methylsulfonyl)-2-nitroanilino]methyl}cyclohexanol |
| [N+](=O)([O-])c1c(ccc(c1)c3n[o]c(n3)C)NCc2[o]ccc2 | Vitas-M | 300.27 | N-(2-furylmethyl)-4-(5-methyl-1,2,4-oxadiazol-3-yl)-2-nitroaniline |
| [S](=O)(=O)©c1cc(c(cc1)NCc2n]3c(nn2)CCC3)[N+](=O)[O-] | Enamine | 337.36 | N-(6,7-dihydro-5H-pyrrolo[2,1-c][1,2,4]triazol-3-ylmethyl)-N-[4-(methylsulfonyl)-2-nitrophenyl]amine |
| Clc1c(ccc(c1)[N+](=O)[O-])NCc2cc(c(cc2)OC)OC | Enamine | 322.75 | 2-chloro-N-(3,4-dimethoxybenzyl)-4-nitroaniline |
| Fc1c(ccc(c1)[N+](=O)[O-])NCc2ccc(cc2)C(O)C | Enamine | 290.29 | 1-{4-[(2-fluoro-4-nitroanilino)methyl]phenyl}ethanol |
| [N+](=O)([O-])c1ccc(cc1)O[C@@H]2O[C@@H][[C@H]([C@@H]([C@H]2O)O)O)CO | Sigma-Aldrich | 301.25 | 4-nitrophenyl beta-D-glucopyranoside |
| [N+](=O)([O-])c1c(ccc(c1)C(=O)C)NCCc2c(ccc(c2)C)O | Enamine | 328.37 | 1-(4-{[2-(2-methoxy-5-methylphenyl)ethyl]amino}-3-nitrophenyl)ethanone |
| Clc1c(ccc(c1)[N+](=O)[O-])NCc2c(ccc(c2)OC)OC | Enamine | 322.75 | 2-chloro-N-(2,5-dimethoxybenzyl)-4-nitroaniline |
| [N+](=O)([O-])c1c(ccc(c1)OC)NC(=O)N2CCC(CC2)O | Enamine | 295.3 | 4-hydroxy-N-(4-methoxy-2-nitrophenyl)-1-piperidinecarboxamide |
| [S](=O)(=O)(NC)c1cc(c(cc1)Nc2cnc(cc2)N©C)[N+](=O)[O-] | Enamine | 351.39 | 4-{[6-(dimethylamino)-3-pyridinyl]amino}-N-methyl-3-nitrobenzenesulfonamide |
| [S]1(=O)(=O)N=C(c3c1cc(cc3)[N+](=O)[O-])Nc2cc(ccc2)N | Vitas-M | 318.31 | |
| [S](=O)(=O)©c1cc(c(cc1)NC©c2cc3c(cc2)OCO3)[N+](=O)[O-] | Enamine | 364.38 | N-{1-(1,3-benzodioxol-5-yl)ethyl]-4-(methylsulfonyl)-2-nitroaniline |

FIG. 9 (cont.)

| SMILES | Supplier | MW | CHEM_NAME |
|---|---|---|---|
| [N+](=O)([O-])c1cc(c(cc1)NCc2nc(n[o]2)C(OCC)C)C#N | Enamine | 317.3 | 2-({[3-(1-ethoxyethyl)-1,2,4-oxadiazol-5-yl]methyl}amino)-5-nitrobenzonitrile |
| [N+](=O)([O-])c1c(ccc(c1)C#N)NC2CCCC(CC2)O | Enamine | 261.28 | 4-[(4-hydroxycyclohexyl)amino]-3-nitrobenzonitrile |
| [N+](=O)([O-])c1c(ccc(c1)[O-])c1c(ccc(c1)[N+](=O)[O-])NC(C(O)C)C(=O)O | Sigma-Aldrich | 285.21 | 2-(2,4-dinitroanilino)-3-hydroxybutanoic acid |
| [S](=O)(=O)(C)c1cc(c(cc1)NCC2N(CCC2)CC)[N+](=O)[O-] | Enamine | 327.4 | N-[(1-ethyl-2-pyrrolidinyl)methyl]-4-(methylsulfonyl)-2-nitroaniline |
| [N+](=O)([O-])c1ccc(cc1)N[C@@H]2O[C@@H]([C@H]([C@@H]([C@@H]2O)O)O)CO | Vitas-M | 300.27 | N-(4-nitrophenyl)-beta-D-mannopyranosylamine |
| Brc1c(cc(c(c1)NCC(O)C(O)C(O)CO)[N+](=O)[O-])C | Sigma-Aldrich | 365.18 | 1-(5-bromo-4-methyl-2-nitroanilino)-1-deoxy-D-ribitol |
| [N+](=O)([O-])c1cc(ccc1NCc2ccc(cc2)C(=O)OC)C(=O)OC | Enamine | 344.32 | methyl 2-{[4-(methoxycarbonyl)benzyl]amino}-5-nitrobenzoate |
| [s]1c(nc(c1)CNc2c(cc(cc2)C(=O)NC)[N+](=O)[O-])NC | Enamine | 321.36 | N-methyl-4-({[2-(methylamino)-1,3-thiazol-4-yl]methyl}amino)-3-nitrobenzamide |
| [S](=O)(=O)(C)c1cc(c(cc1)Nc2cc(cc(c2)OC)OC)[N+](=O)[O-] | Enamine | 352.37 | N-(3,5-dimethoxyphenyl)-4-(methylsulfonyl)-2-nitroaniline |
| [N+](=O)([O-])c1c(ccc(c1)C(=O)C)NCCc2c3c([nH]c2O)cccc3 | Enamine | 339.35 | 3-[2-(4-acetyl-2-nitroanilino)ethyl]-1,3-dihydro-2H-indol-2-one |
| [S]1(=O)(=O)N=C(c3c1cc(cc3)[N+](=O)[O-])Nc2c(ccc(c2)OC)OC | Vitas-M | 363.35 | N-(2,5-dimethoxyphenyl)-6-nitro-1,2-benzisothiazol-3-amine 1,1-dioxide |
| S1c2[n](cc(n2)CNc3c(cc(cc3)C(=O)OC)[N+](=O)[O-])C=C1 | Enamine | 332.34 | methyl 4-[(imidazo[2,1-b][1,3]thiazol-6-ylmethyl)amino]-3-nitrobenzoate |
| [S](=O)(=O)(NC)c1cc(c(cc1)NCC2Oc3c(cc(cc3)OC2)[N+](=O)[O-] | Enamine | 379.39 | 4-[(2,3-dihydro-1,4-benzodioxin-2-ylmethyl)amino]-N-methyl-3-nitrobenzenesulfonamide |

FIG. 9 (cont.)

| SMILES | Supplier | MW | CHEM_NAME |
|---|---|---|---|
| [n]2(cnc(c2N)C(=O)N)C1OC(C(C1O)O)CO | AMS Private | 258.23 | 5-amino-1-(3,4-dihydroxy-5-(hydroxymethyl)tetrahydrofuran-2-yl)-1H-imidazole-4-carboxamide |
| [S]1(=O)(=O)N=C(c3c1cc(cc3)[N+](=O)[O-])Nc2cc(cc2)C(=O)C | Vitas-M | 345.34 | 1-{3-[(6-nitro-1,1-dioxido-1,2-benzisothiazol-3-yl)amino]phenyl}ethanone |
| Clc1ccc(cc1)C(O)CNc2c(cc(cc2)C(=O)C)[N+](=O)[O-] | Enamine | 334.76 | 1-(4-{[2-(4-chlorophenyl)-2-hydroxyethyl]amino}-3-nitrophenyl)ethanone |
| [S](=O)(=O)@c1c(ccc(c1)[S](=O)(=O)NC2OCCC2)C2OCCC2 | Enamine | 333.43 | 2,4-bis(methylsulfonyl)-N-(tetrahydro-2-furanylmethyl)aniline |
| Clc1c(ccc(c1)[N+](=O)[O-])NCc2c(nc(cc2C)C)O | Enamine | 307.74 | 3-[(2-chloro-4-nitroanilino)methyl]-4,6-dimethyl-2-pyridinol |
| Fc1c(c(cc(c1)C(=O)OC)[N+](=O)[O-])NCC2OCCC2 | Enamine | 298.27 | methyl 3-fluoro-5-nitro-4-[(tetrahydro-2-furanylmethyl)amino]benzoate |
| Fc1c(ccc(c1)CNc2c(cc(cc2)F)[N+](=O)[O-])CO | Enamine | 294.26 | {2-fluoro-4-[(4-fluoro-2-nitroanilino)methyl]phenyl}methanol |
| Clc1c(cccc1)CNc2c(cc(cc2)[N+](=O)[O-])C(=O)O | Enamine | 306.71 | 2-[(2-chlorobenzyl)amino]-5-nitrobenzoic acid |
| [N+](=O)([O-])c1cc(ccc1)C(=O)OCCNCc2ccc(cc2)OC | ChemDiv | 330.34 | ethyl 4-[(4-methoxybenzyl)amino]-3-nitrobenzoate |
| [N+](=O)([O-])c1c(ccc(c1)C(=O)OC)NCc2ncc3[n](c2)C=CC=C3 | Enamine | 326.31 | methyl 4-[imidazo[1,2-a]yridine-2-ylmethyl)amino]-3-nitrobenzoate |
| [N+](=O)([O-])c1cc(c(cc1)NCc2c(cc(cc2)OC)OC)C | Vitas-M | 302.33 | N-(2,4-dimethoxybenzyl)-2-methyl-4-nitroaniline |
| Clc1ccc(cc1)CN[C@@H]2OC([C@H](C(C2)O)O)CO | ChemDiv | 303.74 | N-(4-chlorobenzyl)-beta-D-glycero-hexopyranosylamine |
| Fc1ccc(cc1)CNc2c(cc(cc2)C(=O)N)[N+](=O)[O-] | Enamine | 289.27 | 4-[(4-fluorobenzyl)amino]-3-nitrobenzamide |
| [N+](=O)([O-])c1cc(c(cc1)NCc2ccc(cc2)OC)C#N | Enamine | 283.29 | 2-[(4-methoxybenzyl)amino]-5-nitrobenzonitrile |

FIG. 9 (cont.)

| SMILES | Supplier | MW | CHEM_NAME |
|---|---|---|---|
| [N+](=O)([O-])c1c(ccc(c1)C(=O)O)Nc2ccc(cc2)C | Vitas-M | 272.26 | 3-nitro-4-(4-toluidino)benzoic acid |
| [N+](=O)([O-])c1cc(c(cc1)N\C=C2/CCCC/2=O)OC | Vitas-M | 262.27 | (2E)-2-[(2-methoxy-4-nitroanilino)methylene]cyclopentanone |
| FC(F)(F)c1cc(c(cc1)NCc2ccc(cc2)OC)[N+](=O)[O-] | Enamine | 326.28 | N-(4-methoxybenzyl)-2-nitro-4-(trifluoromethyl)aniline |
| S(c2nc(cc(n2)O)N)c1c(cc(cc1)C(=O)C)[N+](=O)[O-] | Labotest | 306.3 | 1-{4-[(4-amino-6-hydroxy-2-pyrimidinyl)sulfanyl]-3-nitrophenyl}ethanone |
| [N+](=O)([O-])c1c(ccc(c1)C(=O)N)NCc2ccc(cc2)C | Enamine | 285.3 | 4-[(4-methylbenzyl)amino]-3-nitrobenzamide |
| [S](=O)(=O)©c1cc(c(cc1)Sc2nc(cc(n2)C)C)[N+](=O)[O-] | Enamine | 339.4 | 4,6-dimethyl-2-[[4-(methylsulfonyl)-2-nitrophenyl]sulfanyl]pyrimidine |
| *[S](=O)(=O)©c1cc(c(cc1)Nc2ccc3c(cc2)OCO3)[N+](=O)[O-]* | *Enamine* | *339.33* | *N-[4-(methylsulfonyl)-2-nitrophenyl]-1,3-benzodioxol-5-amine, MSNBA* |
| [N+](=O)([O-])c1c(ccc(c1)C(=O)O)NCCC2=CCCCC2 | ChemDiv | 290.32 | 4-{[2-(1-cyclohexen-1-yl)ethyl]amino}-3-nitrobenzoic acid |
| [N+](=O)([O-])c1cc(c(cc1)NCc2cnccc2)C(=O)O | ChemBridge | 273.25 | 5-nitro-2-[(3-pyridinylmethyl)amino]benzoic acid |
| [S](=O)(=O)(N)c1cc(c(cc1)NCc2ccccc2)[N+](=O)[O-] | ChemBridge | 307.33 | 4-(benzylamino)-3-nitrobenzenesulfonamide |
| [S](=O)(=O)©c1cc(c(cc1)NC©c2[s]ccc2)[N+](=O)[O-] | Enamine | 326.4 | 4-(methylsulfonyl)-2-nitro-N-[1-(2-thienyl)ethyl]aniline |
| Clc1ccc(cc1)CNc2c(cc(cc2)C(=O)N)[N+](=O)[O-] | Enamine | 305.72 | 4-[(4-chlorobenzyl)amino]-3-nitrobenzamide |
| Fc1c(ccc(c1)[N+](=O)[O-])NCc2cc(c(cc2)CO)F | Enamine | 294.26 | {2-fluoro-4-[(2-fluoro-4-nitroanilino)methyl]phenyl}methanol |
| [N+](=O)([O-])c1c(ccc(c1)C(=O)C)NCC2CCN(CC2)CC | Enamine | 305.38 | 1-(4-{[(1-ethyl-4-piperidinyl)methyl]amino}-3-nitrophenyl)ethanone |
| [N+](=O)([O-])c1c(ccc(c1)C(=O)C)NCc2cc(ncc2)OC | Enamine | 301.3 | 1-(4-{[(2-methoxy-4-pyridinyl)methyl]amino}-3-nitrophenyl)ethanone |

FIG. 9 (cont.)

| SMILES | Supplier | MW | CHEM_NAME |
|---|---|---|---|
| Fc1c(ccc(c1)CNc2c(cc(cc2)[N+](=O)[O-])Cl)CO | Enamine | 310.71 | {4-[(2-chloro-4-nitroanilino)methyl]-2-fluorophenyl}methanol |
| [N+](=O)([O-])c1cc(c(cc1)NCC2Oc3c(cccc3)OC2)C(=O)OC | Enamine | 344.32 | methyl 2-[(2,3-dihydro-1,4-benzodioxin-2-ylmethyl)amino]-5-nitrobenzoate |
| Clc1c(c(cc(c1)Cl)C(=O)Nc2c(cc(cc2)[N+](=O)[O-])OC)O | Vitas-M | 357.15 | 3,5-dichloro-2-hydroxy-N-(2-methoxy-4-nitrophenyl)benzamide |
| [S](=O)(=O)(@c1cc(c(cc1)NCC2(CCC2)O)[N+](=O)[O-]) | Enamine | 300.34 | 1-{[(4-(methylsulfonyl)-2-nitroanilino]methyl}cyclobutanol |
| [N+](=O)([O-])c1cc(c(cc1)N\C=C2\CCCCC2=O)OC | ChemBridge | 276.29 | (2Z)-2-[(2-methoxy-4-nitroanilino)methylene]cyclohexanone |
| Clc1cc(c(cc1)O)C(=O)Nc2c(cc(cc2)OC)[N+](=O)[O-] | Sigma-Aldrich | 322.7 | 5-chloro-2-hydroxy-N-(4-methoxy-2-nitrophenyl)benzamide |
| [s]1c(nc(c1CC(=O)Nc2c(cc(cc2)OCC)[N+](=O)[O-])O)N | Vitas-M | 338.34 | N-(4-ethoxy-2-nitrophenyl)-2-(2-imino-4-oxo-1,3-thiazolidin-5-yl)acetamide |
| [S](=O)(=O)(NC)c1cc(c(cc1)NCc2cc(ncc2)OC)[N+](=O)[O-] | Enamine | 352.37 | 4-{[(2-methoxy-4-pyridinyl)methyl]amino}-N-methyl-3-nitrobenzenesulfonamide |
| [N+](=O)([O-])c1cc(c(cc1)NCc2cc(ccc2)OCC)C#N | Enamine | 297.31 | 2-[(3-ethoxybenzyl)amino]-5-nitrobenzonitrile |
| [s]1c(nc(c1CC(=O)Nc2c(cc(cc2)OC)[N+](=O)[O-])O)N | Vitas-M | 324.32 | 2-(2-imino-4-oxo-1,3-thiazolidin-5-yl)-N-(4-methoxy-2-nitrophenyl)acetamide |
| [N+](=O)([O-])c1cc(ccc1)C(=O)OCC)NCc2c(cccc2)OC | ChemDiv | 330.34 | ethyl 4-[(2-methoxybenzyl)amino]-3-nitrobenzoate |
| FC(F)(F)c1cc(c(cc1)NC2CCC(CC2)O)[N+](=O)[O-] | Enamine | 304.27 | 4-[2-nitro-4-(trifluoromethyl)  niline]cyclohexanol |
| [N+](=O)([O-])c1cc(c(cc1)NC2OC(C(C2)O)CO)C | ChemBridge | 268.27 | 2-deoxy-N-(2-methyl-4-nitrophenyl)pentofuranosylamine |
| Fc1c(cccc1)C(O)CNc2c(cc(cc2)C(=O)C)[N+](=O)[O-] | Enamine | 318.3 | 1-(4-{[2-(2-fluorophenyl)-2-hydroxyethyl]amino}-3-nitrophenyl)ethanone |

FIG. 9 (cont.)

| SMILES | Supplier | MW | CHEM_NAME |
|---|---|---|---|
| [s]1c(nnc1N)Sc2c(cc(cc2)[N+]( =O)[O-])C(=O)O | Labotest | 298.3 | 2-[(5-amino-1,3,4-thiadiazol-2-yl)sulfanyl]-5-nitrobenzoic acid |
| Clc1c(cccc1)CCNc2c(cc(cc2)C(=O)O)[N+](=O)[O-] | ChemDiv | 320.73 | 4-[[2-(2-chlorophenyl)ethyl]amino]-3-nitrobenzoic acid |
| [N+](=O)([O-])c1cc(c(cc1)NCc2cnccc2)C(=O)N | Vitas-M | 272.26 | 5-nitro-2-[(3-pyridinylmethyl)amino]benzamide |
| Fc1ccc(cc1)CNc2c(cc(cc2)C(=O)OCC)[N+](=O)[O-] | ChemDiv | 318.3 | ethyl 4-[(4-fluorobenzyl)amino]-3-nitrobenzoate |
| [S](=O)(=O)(c1cc(c(cc1)NC@c2ccccc2)[N+](=O)[O-] | Vitas-M | 320.37 | 4-(methylsulfonyl)-2-nitro-N-(1-phenylethyl)aniline |
| [n]2(ncnc2)C1OC(C(C1O)O)COC | AMS Private Supplier 1 | 215.21 | |
| O1[C@H]C(C(C1CO)O)O)Occ2ccccc2 | Sigma-Aldrich | 240.26 | benzyl beta-D-ribofuranoside |
| [S](=O)(=O)@c1cc(c(cc1)Sc2[s]cc(n2)C)[N+](=O)[O-] | Enamine | 330.41 | methyl 4-[(4-methyl-1,3-thiazol-2-yl)sulfanyl]-3-nitrophenyl sulfone |
| Fc1c(ccc(c1)[N+](=O)[O-])NCC2OCCC2 | Enamine | 240.23 | N-(2-fluoro-4-nitrophenyl)-N-(tetrahydro-2-furanylmethyl)amine |
| [S](=O)(=O)@c1c(ccc(c1)[S](=O)(=O)C)NCC2OCCC2 | Enamine | 347.46 | 2,4-bis(methylsulfonyl)-N-(2-tetrahydro-2-furanylethyl)aniline |
| Clc1c(ccc(c1)[N+](=O)[O-])NCc2ncccc2 | Enamine | 263.68 | 2-chloro-4-nitro-N-(2-pyridinylmethyl)aniline |
| [N+](=O)([O-])c1c(cccc1)O[C@@H]2O[C@@H]([C@H]([C@@H]([C@H]2O)O)O)CO | Sigma-Aldrich | 301.25 | 2-nitrophenyl beta-D-glucopyranoside |
| Clc1c(c(cc(c1)Cl)C(=O)Nc2c(cc(cc2)OC)[N+](=O)[O-])O | Sigma-Aldrich | 357.15 | 3,5-dichloro-2-hydroxy-N-(4-methoxy-2-nitrophenyl)benzamide |
| [N+](=O)([O-])c1cc(c(cc1)NC2CCC(CC2)O)C#N | Enamine | 261.28 | 2-[(4-hydroxycyclohexyl)amino]-5-nitrobenzonitrile |

FIG. 9 (cont.)

| SMILES | Supplier | MW | CHEM_NAME |
|---|---|---|---|
| [S](=O)(=O)(NC)c1cc(c(cc1)NC@c2cc3c(c2)OCO3)[N+](=O)[O-] | Enamine | 379.39 | 4-{[1-(1,3-benzodioxol-5-yl)ethyl]amino}-N-methyl-3-nitrobenzenesulfonamide |
| Fc1cc(c(cc1)NCc2nc([s]c2)NC)[N+](=O)[O-] | Enamine | 282.3 | N-{4-[(4-fluoro-2-nitroanilino)methyl]-1,3-thiazol-2-yl}-N-methylamine |
| Clc1c(cc(c(c1)[N+](=O)[O-])NCC(O)C(O)CO)CC | Sigma-Aldrich | 334.76 | 1-(4-chloro-5-ethyl-2-nitroanilino)-1-deoxypentitol |
| [N+](=O)[O-]c1c(ccc(c1)C(=O)C)NCC2N(CCC2)C | Enamine | 277.32 | 1-(4-{[(1-methyl-2-pyrrolidinyl)methyl]amino}-3-nitrophenyl)ethanone |
| [s]1c(nc(c1)C)Sc2c(cc(cc2)[N+](=O)[O-])C(=O)O | Enamine | 296.33 | 2-[(4-methyl-1,3-thiazol-2-yl)sulfanyl]-5-nitrobenzoic acid |
| [N+](=O)[O-]c1c(ccc(c1)C(=O)C)NCCc2ccc(cc2)OC | Enamine | 314.34 | 1-(4-{[2-(4-methoxyphenyl)ethyl]amino}-3-nitrophenyl)ethanone |
| FC(F)(F)c1cc(c(cc1)NCC(CO)Cc2[o]ccc2)[N+](=O)[O-] | Enamine | 344.29 | 3-(2-furyl)-2-{[2-nitro-4-(trifluoromethyl) aniline]methyl}-1-propanol |
| S(c2nc(cc(n2)O)O)c1c(cc(cc1)C(=O)N)[N+](=O)[O-] | Labotest | 308.27 | 4-[(4,6-dihydroxy-2-pyrimidinyl)sulfanyl]-3-nitrobenzamide |
| FC(F)(F)c1cc(c(cc1)NCc2cc(c(cc2)OC)Cl)[N+](=O)[O-] | Key Organics / BIONET | 360.72 | N-(3-chloro-4-methoxybenzyl)-2-nitro-4-(trifluoromethyl)aniline |
| [N+](=O)[O-]c1c(ccc(c1)c3nc(n[o]3)C)NCC2OCCC2 | ChemDiv | 304.31 | 4-(3-methyl-1,2,4-oxadiazol-5-yl)-2-nitro-N-(tetrahydro-2-furanylmethyl)aniline |
| [S](=O)(=O)©c1cc(c(cc1)NCCc2ccccc2)[N+](=O)[O-] | Enamine | 320.37 | 4-(methylsulfonyl)-2-nitro-N-(2-phenylethyl)aniline |
| S(c2nc(cc(n2)O)N)c1c(cc(cc1)C(=O)N)[N+](=O)[O-] | Labotest | 307.29 | 4-[(4-amino-6-hydroxy-2-pyrimidinyl)sulfanyl]-3-nitrobenzamide |
| N(C2OC(C(C(C2O)O)O)CO)c1ncccc1 | Vitas-M | 256.26 | N-(2-pyridinyl)hexopyranosylamine |
| O1[C@H]([C@@H]([C@@H]([C@@H]([C@H]1CO)O)O)Oc2ccccc2 | Sigma-Aldrich | 256.26 | phenyl beta-D-glucopyranoside |

FIG. 9 (cont.)

| SMILES | Supplier | MW | CHEM_NAME |
|---|---|---|---|
| [S](=O)(=O)(OC)O.N2(C=CC(=N)N(C2=O)C)[C@@H]1O[C@@H]([C@H]([C@H]1O)O)CO | Sigma-Aldrich | 369.35 | 1-((2R,3R,4S,5R)-3,4-dihydroxy-5-(hydroxymethyl)tetrahydrofuran-2-yl)-4-imino-3-methyl-3,4-dihydropyrimidin-2(1H)-one methyl sulfate |
| Brc1ccc(cc1)N[C@@H]2OC[C@H](C(C2O)O)O | Vitas-M | 304.14 | N-(4-bromophenyl)-beta-D-glycero-pentopyranosylamine |
| [N+](=O)([O-])c1cc(ccc1)NC2OC(C(C2O)O)CO | Vitas-M | 270.24 | N-(3-nitrophenyl)pentofuranosylamine |
| S([C@@H]2O[C@@H]([C@H]([C@@H]([C@H]2O)O)O)CO)c1ccc(cc1)C | Sigma-Aldrich | 286.35 | 4-methylphenyl 1-thio-beta-D-glucopyranoside |
| [N+](=O)([O-])c1ccc(cc1)O[C@@H]2O[C@H]([C@@H]([C@@H]2O)O)CO | Sigma-Aldrich | 271.23 | 4-nitrophenyl alpha-L-arabinofuranoside |

HUMAN GLUT5 SPECIFIC INHIBITORS AND METHODS OF TREATMENT

This application is a United States national phase patent application based upon International patent application no. PCT/US2016/036872 filed Jun. 10, 2016, which claims the benefit of priority of U.S. provisional application No. 62/174,630, filed Jun. 12, 2015, of identical title, all of which said applications are incorporated by reference in their entirety herein.

RELATED APPLICATIONS AND GRANT SUPPORT

This invention was made with government support under R01 DK091754 and U54 CA189205 awarded by the National Institutes of Health (NIH). The government has certain rights in the invention.

FIELD OF THE INVENTION

The present invention relates to compounds which have been discovered to be potent ligands (inhibitors) of the fructose-only transporter GLUT5 (encoded in humans by the SLC2A5 gene), a facilitative transporter that is specific for fructose, and their use as ligands in assays which can uncover additional ligands of GLUT5, having the potential for being used as drugs. In addition, the present invention is directed to compounds, chemical compositions and methods for treating disease states and conditions which are mediated through GLUT5, including such disease states and conditions as GLUT5 deficiency syndrome, diabetes (type I and II), cancer, metabolic diseases including metabolic syndrome and non-alcoholic fatty liver disease, among others. In further aspects, the present invention is directed to the use of GLUT5 inhibitors for reducing the absorption of fructose from food compositions, methods of inhibiting fructose absorption and food compositions comprising fructose and a GLUT5 inhibitor in an amount effective to substantially inhibit the absorption of fructose from the intestines of a patient or subject.

BACKGROUND AND DESCRIPTION OF THE INVENTION

Fructose is one of the most common dietary carbohydrates. Humans used to get relatively small amounts of fructose during their evolution, mostly from fruits. Recent studies indicate that fructose consumption increased by almost 50% among US adults in the last 30 years, with fructose accounting for at least 10% of daily calories on average[1]. Unlike glucose, fructose in serum is not regulated by insulin, so high-levels of fructose consumption can cause dyslipidemia, impair glucose homeostasis and increase insulin resistance[2]. Some studies also link a fructose rich diet with high blood pressure[3].

Fructose transport across cell membranes is carried out by members of the facilitated glucose transporter (GLUT, SLC2) family. Among 14 members of human GLUT protein family, only GLUT5 is fructose specific, lacking the ability to transport other carbohydrates like glucose and galactose[4,5]. GLUT5 is expressed in intestine (largest relative expression in jejunum and duodenum), sperm, brain, fat, skeletal muscle and kidney cells[6]. Expression of GLUT5 under normal conditions is upregulated by fructose[7]. As the only apical membrane fructose transporter in the small intestine, GLUT5 is essential for fructose absorption.

GLUT5 is linked with various pathologies. In diabetic patients, GLUT5 expression in muscle cells increased, with GLUT5 mRNA level 82% higher than in healthy individuals. Although GLUT5 was not reported to be insulin dependent, drugs that enhance insulin action affected GLUT5 expression rate[8]. In mice lines that exhibit high blood pressure, GLUT5 is down regulated in the intestine[9]. Cancer cells require more energy for their uncontrolled growth and usually show increased rates of carbohydrates transport, compared to normal cells. GLUT5 is frequently overexpressed in cancer cells (~27% of analyzed tumors)[10]. Significantly, while GLUT5 is not normally present in mammalian breast cells, the breast carcinoma cell lines MCF-7 and MDA-MB-231 exhibit elevated GLUT5 mRNA level and show high rates of fructose transport[11]. This may allow the use of GLUT5 as a marker for cancer. Given the medical importance of GLUT5, its inhibitors have the potential to become drugs for treatment of cancer or diabetes.

Viable drugs that target fructose transport of GLUT5 should not interfere with glucose transport of other GLUT proteins. For instance, disrupting glucose transport by the insulin-dependent GLUT4 can lead to diabetes[12]. GLUT1, another transporter of glucose, is expressed in most tissues, so its inhibition can cause serious side effects at the organism level. Therefore inhibitors specific for GLUT5 would ideally affect only tissues where GLUT5 is overexpressed, without altering aspects of metabolism unrelated to fructose consumption. Nonetheless, selective inhibitors for GLUT5 are yet to be described. Despite the high sequence similarity among GLUT members, known inhibitors of other GLUT proteins do not affect GLUT5 suggesting that subtle differences may be responsible for ligand specificity.

Recently the crystal structures of GLUT1[13] and of two bacterial GLUT homologues, XylE[14] and GlcP$_{Se}$[15] were solved. Glucose transporters GLUT1 and GlcP$_{Se}$ share 75% and 67% sequence homology with GLUT5, respectively. To determine inhibitors for GLUT5, we modeled GLUT5 on the basis of GlcP$_{Se}$ crystal structure (PDB ID 4LDS) and used the model to screen in silico a library of small compounds, for binding to GLUT5. The top ranked 175 candidates were checked for inhibition of fructose transport by human GLUT5 in proteoliposomes. We found that N-[4-(methylsulfonyl)-2-nitrophenyl]-1,3-benzodioxol-5-amine (MSNBA, SMILES: [S](=O)(=O)(C)c1cc(c(cc1)Nc2cc3c (cc2)OCO3)[N+](=O)[O—]) is an inhibitor of GLUT5.

MSNBA did not affect the transport activity of either GLUT1 or GlcP$_{Se}$, appearing to be specific for GLUT5. Docking of MSNBA to the GLUT5 model, along with mutagenesis and functional studies on GLUT5, GLUT1 and GlcP$_{Se}$, suggested that the inhibitor bound at the active site and pinpointed a GLUT5-specific His residue as a key player in MSNBA recognition. MSNBA together with the active-site differences between GLUT5 and GLUT1 highlighted by MSNBA inhibition can be exploited in rationally designing potent, specific inhibitors for GLUT5 that will aid in cancer or diabetes treatment.

BRIEF DESCRIPTION OF THE FIGURES

FIG. 1 shows the chemical structure of five ligands of GLUT5 which have been identified and are used in the present invention.

FIG. 4 shows the modeled interaction of MSNBA with GLUT5. (a) Binding of MSNBA to the transmembrane site in GLUT5 as predicted by docking of inhibitor to GLUT5 model with MOE. The figure was drawn with Molscript[41] and raster3D[42]. (b) Interactions between MSNBA and side chains of GLUT5. Interacting residues come from helices 4 (S143), 5 (T171), 7 (Q288, Q289, N294 and Y297), and 10 (H387); see also Supplementary FIG. 1. (c) Multiple sequence alignment among GLUT homologues for the GLUT5 residues predicted to interact with MSNBA. Alignment was generated with ClustalW[43].

FIG. 9, shows a list of the compounds which were screened for GLUT5 activity. Compounds in italics are GLUT5 inhibitors (see FIG. 1). MSNBA is shown in bold italics.

BRIEF DESCRIPTION OF THE INVENTION

In one embodiment, the present invention is directed to fourteen (14) compounds which have been discovered to be potent ligands/modulators of human GLUT5. These compounds are:

N-[4-(methylsulfonyl)-2-nitrophenyl]-1,3-benzodioxol-5-amine (MSNBA), the preferred compound of the present invention;

N-(2,5-dimethoxybenzyl)-N-[4-(methylsulfonyl)-2-nitrophenyl]amine (FIG. 1);

N-(3,4-dimethoxyphenyl)-4-(methylsulfonyl)-2-nitroaniline (FIG. 1);

N-[1-(3-fluoro-4-methoxyphenyl)ethyl]-4-(methylsulfonyl)-2-nitroaniline (FIG. 1);

N-[1-(1,3-benzodioxol-5-yl)ethyl]-4-(methylsulfonyl)-2-nitroaniline (FIG. 1); and N-(3,5-dimethoxyphenyl)-4-(methylsulfonyl)-2-nitroaniline (FIG. 1), or a pharmaceutically acceptable salt, solvate or polymorph thereof.

Figure 2:
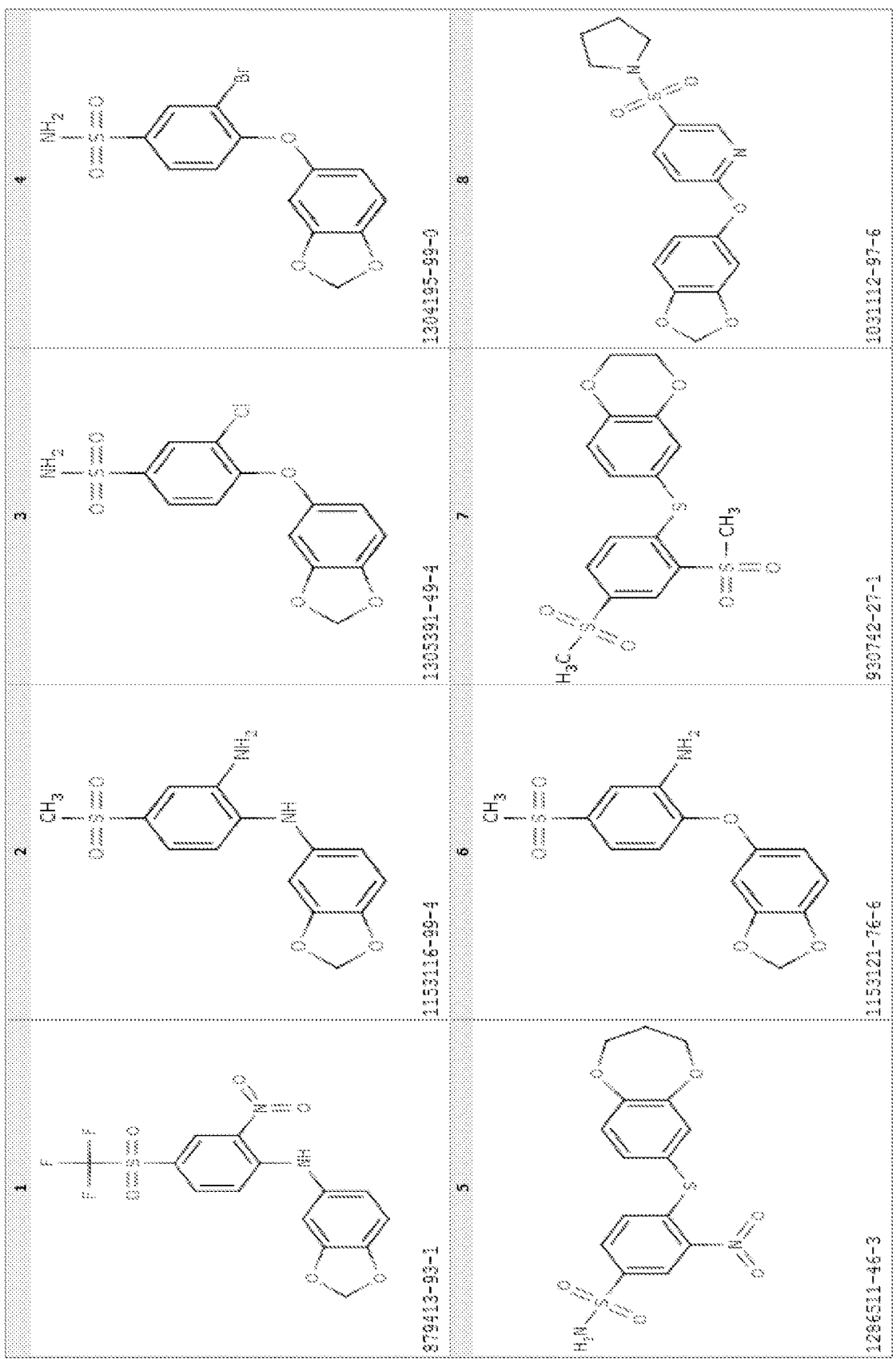
FIG. 2 shows the chemical structure of eight additional ligands of GLUT5 which have been identified and are used in the present invention.

The remaining eight (8) compounds appear in attached FIG. 2, hereof or a pharmaceutically acceptable salt, solvate or polymorph thereof. They are presented below.

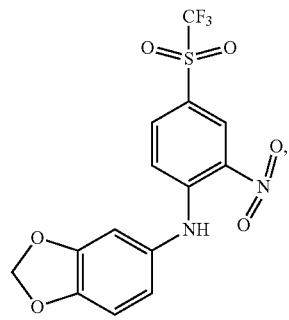

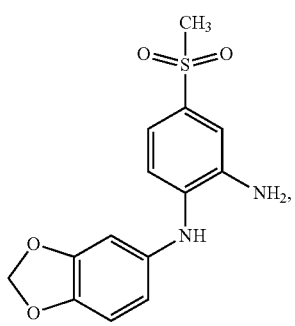

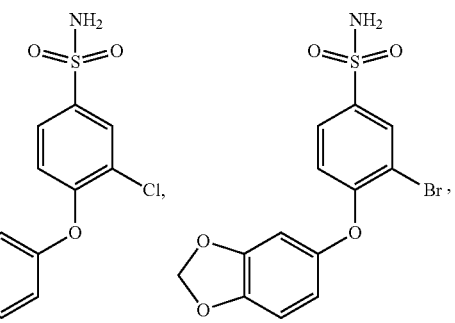

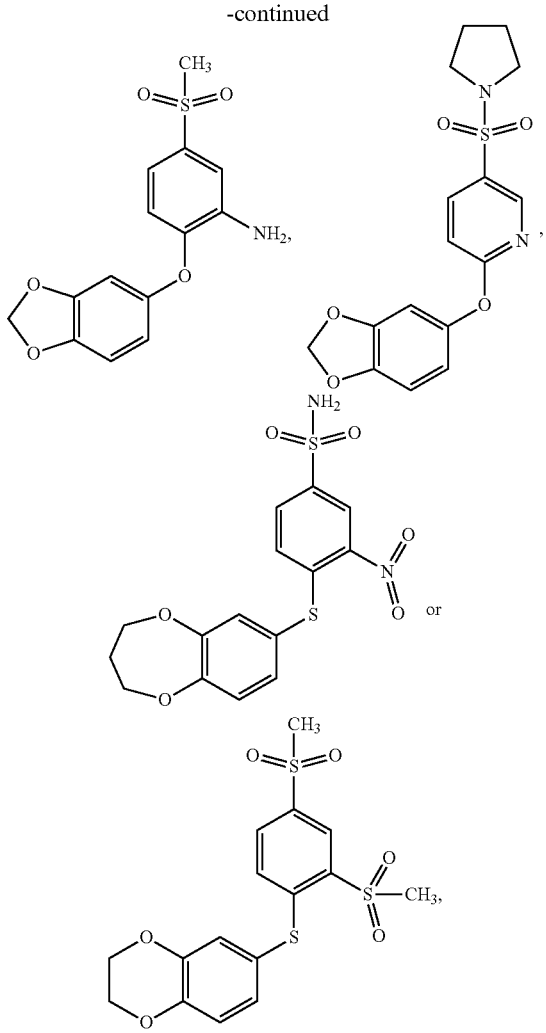

or a pharmaceutically acceptable salt, solvate or polymorph thereof.

The preferred ligand of human GLUT5 of the present invention, MSNBA, has the following chemical structure:

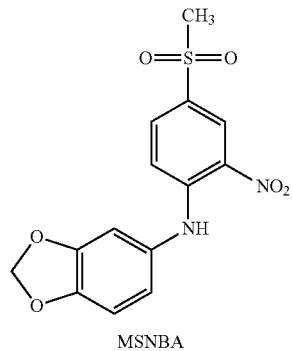 [SMILES: CS(=O)(=O)c1ccc(Nc2ccc3c(c2)OCO3)c([N+](=O)[O-])c1]

MSNBA or a pharmaceutically acceptable salt, thereof.

The remaining ligands, a number of which identified are identified above, have chemical structures, which are presented in attached FIGS. 1 and 2 hereof.

In another embodiment, the present invention is directed to pharmaceutical compositions comprising an effective amount of a GLUT5 modulator in combination with a pharmaceutically acceptable carrier, additive or excipient and optionally at least one additional bioactive agent as otherwise described herein.

In still another embodiment, the present invention is directed to a method for treating a disease state or condition which is mediated through GLUT5 comprising administering to a patient in need thereof an effective amount of at least one GLUT 5 modulator, preferably MSNBA, optionally in combination with an additional bioactive agent. In this embodiment, the disease states and/or conditions which are favorably treated include GLUT5 deficiency syndrome, diabetes (type I and II), cancer, metabolic diseases including metabolic syndrome and fatty liver disease, including non-alcohol fatty liver disease (NALFD). In preferred embodiments, the additional bioactive agent is also useful in treating or reducing the likelihood of a disease state or condition which is mediated through GLUT5.

In yet an additional embodiment, one or more of the GLUT5 modulators in useful as a ligand in GLUT5 assays for identifying the GLUT5 activity of compounds whose GLUT5 activity is unknown.

In another embodiment, the present invention is directed to a food composition which comprises fructose and an amount of a GLUT5 inhibitor which is effective for reducing the absorption of fructose from the gastrointestinal tract (generally, enterocytes in the small intestine) of a patient or subject who has ingested the food composition.

In still a further embodiment, the present invention is directed to a method of reducing the absorption of fructose from a food composition comprising adding to the food composition an effective amount of a GLUT5 inhibitor. In additional embodiments, the GLUT5 inhibitor can be ingested by a subject at approximately the same time as the subject ingesting foods which comprise fructose in order to inhibit the absorption of fructose from the ingested food during digestion.

These and/or other embodiments of the present invention are readily gleaned from a review of the detailed description of the present invention which follows.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts thereof, if applicable. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used, for example, to produce or affect an intended result, often the modulation of GLUT5 within the context of a particular treatment or assay, or alternatively, the effect of a bioactive agent which is coadministered with the GLUT5 modulator in the treatment of disease or in a food composition to facilitate inhibition of absorption of fructose from the foodstuff in the digestive tract of the subject.

The terms "treat", "treating", and "treatment", etc., as used herein, refer to any action providing a benefit to a patient at risk for or afflicted by a GLUT5 mediated disease state or condition as otherwise described herein. The benefit may be in curing the disease state or condition, inhibition its progression, or ameliorating, lessening or suppressing one or more symptom of an autophagy mediated disease state or condition, especially including excessive inflammation caused by the disease state and/or condition. In addition, treatment includes inhibiting fructose absorption from the gastrointestinal tract of a subject who has ingested food with substantial fructose content and incorporating one or more GLUT 5 inhibitors into a food composition comprising fructose for that purposes. Treatment, as used herein, encompasses both prophylactic and therapeutic treatment.

The term "GLUT5 mediated disease state or condition" is used to describe a disease state or condition which is mediated through human GLUT5, i.e., where GLUT5 plays an important role in the development and/or treatment of the disease state or condition to be treated. GLUT5 mediated disease states which are treated using compound and compositions disclosed herein include GLUT5 deficiency syndrome, diabetes (type I and II), cancer, metabolic diseases including metabolic syndrome and fatty liver disease, among others.

The term "additional bioactive agent includes compounds which may be used in combination with a GLUT5 modulator compound according to the present invention in treating a disease state or condition which is mediated through GLUT5, including GLUT5 deficiency syndrome, diabetes (type I and II), cancer, metabolic diseases including metabolic syndrome and fatty liver disease, including non-alcohol fatty liver disease (NALFD). These compounds include anti-cancer agents, as described in detail hereinbelow, or bioactive which are alternative agents for the treatment of diabetes I or II and metabolic diseases including metabolic syndrome and fatty liver disease, including insulin (for type I diabetes), metformin, glipizide, glimepiride, glyburide, bromocriptine, pioglitazone, acarbose, sitagliptin, netaglinide, colesevelam, chlorpropamide, exenatide, liriglutide, repaglinide, rosiglitazone, saxagliptin, linagliptin, canagliflozin, miglitol, tolbutamide, tolazamide, mifepristone, dapagliflozin, pramlintide, alogliptin, albiglutide, empagliflozin, dulaglutide, and mixtures thereof, among others.

Cardiovascular agents, such as agents for hypertensive emergencies, agents for pulmonary hypertension, aldosterone receptor antagonists, angiotensin converting enzyme inhibitors, angiotensin receptor blockers, antiadrenergic agents (peripherally or centrally acting), antianginal agents, antiarrhythmic agents (groups I, II, III, IV, V), anticholinergic chronotropic agents, ACE inhibitors, calcium channel blocking agents, thiazides, beta blockers, potassium sparing diuretics, beta-adrenergic blockers (cardioselective and non-cardioselective), catecholamines, diuretics, inotropic agents, vasodilators, including peripheral vasodilators, miscellaneous cardiovascular agents, renin inhibitors, sclerosing agents, vasopressin antagonists and vasopressors, among others and agents to reduce cholesterol ("statins"), such as rosuvastatin, atorvastain, simvastatin, pravastatin, atorvastatin and fluvastatin are additional bioactive agents which can be co-administered along with GLUT5 modulators (inhibitors) according to the present invention.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. The term cancer also within context, includes drug resistant cancers, including multiple drug resistant cancers and recurrent cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germline tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, among others. It is noted that certain cancers and tumors including especially B-cell lymphoma, pancreatic cancer, lung cancer, stomach cancer including gastric adenocarcinoma, leukemias, including myeloid and B-cell leukemias, breast, cervical, ovarian, testicular and prostate cancer among others may be principal target cancers for compounds and therapies according to the present invention.

The term "anti-cancer agent" is used to describe an additional compound or bioactive agent which may be coadministered with one or more compounds of the present invention in the treatment of cancer. Such agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H -pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291 squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis. The term co-administration also contemplates the ingestion/oral administration of an effective amount of a GLUT5 inhibitor, especially MSNBA, with foods which contain fructose, especially high fructose content foods, in order to substantially reduce the absorption of the fructose from the food during digestion.

The term "food composition" refers to a composition which is ingested as food and which contains an appreciable (at least about 0.1%, 0.5%, 1%, 2%, 5%, 10% or more by weight) amount of fructose in the composition which can be absorbed upon digestion. In certain embodiments, the food composition may contain effective amounts of a GLUT5 inhibitor, especially MSNBA, in an amount effective to reduce the absorption of fructose from the gastrointestinal tract (especially enterocytes in the small intestine) of the subject who has ingested the food composition.

Compounds according to the present invention may be readily formulated into pharmaceutical compositions, useful in the treatment of disease states and conditions and infections as otherwise described hereinabove. Pharmaceutical compositions comprise an effective amount of one or more compounds according to the present invention in combination with a pharmaceutically acceptable carrier, additive or excipient, optionally in combination with at least one additional anticancer agent or other agent effective for the purpose for which the composition is intended. In addition to anticancer agents, the present invention also contemplates the coadministration of an antimicrobial or antifungal agents, depending upon the final use for which the pharmaceutical composition is intended. Typical antimicrobial agents/antibiotics include the aminoglycosides, ansamycins, carbacephems, carbapenems, cephalosporins, glycopeptides, lincosamides, lipopeptides, macrolides, monobacftams, nitrofurans, penicillins, polypeptides, quinolones, sulfonamides, tetracyclines and anti-mycoacterials, among others. Typical antifungal agents include the polyenes, imidazoles, triazoles, thiazoles, allylamines and echinocandins, among others. Other bioactive agents, as otherwise described herein are also contemplated for co-administration with the GLUT5 modulator compounds herein.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

As noted above, the compounds and methods of the invention modulate (generally through inhibition) GLUT 5 as otherwise described herein, and are useful for the inhibition (including prophylaxis) and/or treatment of GLUT5 deficiency syndrome, diabetes (type I and II), cancer, metabolic diseases including metabolic syndrome, fatty liver disease and NASH (non-alcoholic steatohepatitis), among others as described herein above.

In methods according to the present invention, subjects or patients in need are trreated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, effective amounts in the less than milligram (e.g. 250 micrograms) up to gram quantities are employed. Often the effective amount is in the range of about 500 microgram to about 1 gram. The composition may be administered to a subject by various routes, e.g. orally, topically, transdermally, perineurally or parenterally, that is, by intravenous, subcutaneous, intraperitoneal, or intramuscular injection, among others, including buccal, sublingual, rectal, by inhalation and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical additives, carriers and excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or are apparent to those skilled in the art; for example, see *Remington's Pharmaceutical Sciences* (17th Ed., Mack Pub. Co., 1985). The composition to be administered will contain a quantity of the selected compound in a pharmaceutically effective amount for modulating GTPase in a subject according to the present invention in a subject.

Compounds according to the present invention may also be used as ligands of human GLUT5 in assays for drug discovery. These ligands may be used as standards to determine the relative activity of compounds of unknown activity as modulators of GLUT5 for the treatment of disease states which are modulated through GLUT5 such as GLUT5 deficiency syndrome, diabetes (type I and II), cancer, metabolic diseases including metabolic syndrome, fatty liver disease, including non-alcohol fatty liver disease (NALFD) and NASH (non-alcoholic steatohepatitis), among others. Although a number of GLUT5 ligands may be used in this aspects of the invention (see FIGS. 1 and 2), MSNBA is the preferred ligand inasmuch as it exhibits the best binding of GLUT5 and its use as a standard in an assay. Numerous assays which utilize GLUT5 ligand binding and displacement by an unknown compound may be used to identify compounds as being potential modulators (inhibitors or agonists) of GLUT5 because of their displacement of the ligand from GLUT5 in the assay.

The following examples illustrate but are not intended in any way to limit the invention.

EXAMPLES

GLUT5, a facilitative glucose transporter (GLUT, SLC2) family member that transports fructose, is involved in diabetes, obesity and cancer. To identify inhibitors of human GLUT5, the inventors virtually screened a library of 6 million chemicals onto a structural model of GLUT5. The top ranked 175 potential ligands were tested for inhibition of GLUT5 in proteoliposomes. The inventors found that N-[4-(methylsulfonyl)-2-nitrophenyl]-1,3-benzodioxol-5-amine (MSNBA) inhibits GLUT5 with an $IC_{50}$ of 0.10±0.03 mM. MSNBA was specific for GLUT5, as it did not affect the fructose transport of human GLUT2 or the glucose transport of any of the human GLUT1, GLUT3, GLUT4 or bacterial $GlcP_{Se}$. Docking of MSNBA to a GLUT5 model, combined with mutagenesis and functional studies, indicates that MSNBA binds near the active site, and its interaction with H387 is crucial for inhibition specificity. These examples relate to MSNBA as a precursor of specific, improved inhibitors for GLUT5, and pinpoint active-site differences in GLUT members, which could be exploited to enhance ligand specificity.

Methods
Virtual Screening

The 3D model for GLUT5 was built with the Coot software[17], on the basis of $GlcP_{Se}$ crystal structure (PDB ID 4LDS), using amino acid replacement guided by sequence alignments. GLUT5 model was superimposed to the liganded XylE crystal structure (PDB ID 4GC0) to identify possible binding regions for GLUT5 ligands. All amino acid residues in GLUT5 model interacting with bromo-glucose were labeled and used to define the docking binding pocket through the following procedure: fructose molecule was placed in GLUT5 model using coordinates from bromo-glucose of XylE structure, and flexible docking was performed with Molecular Operating Environment (MOE, Chemical Computing Group Inc.), so that both ligand (fructose) and binding pocket residues were allowed to be flexible. Only the top 5 ligand-transporter scoring poses were saved and used with FRED docking[31], given the time constraints of flexible docking on the ChemNavigator library (http://www.chemnavigator.com). The library was prepared for virtual screening as follows. Standard clean up procedure was employed where chemical structures were checked for valence errors, salt and solvent removal. A total of 6,273,384 chemicals were selected for further processing. Standardized chemical structures were then used to calculate 2D extended connectivity fingerprints (ECFP) using an in-house implementation of algorithm described in literature[32]. Conformer generation with Omega[33] prepared input for 3D shape and docking applications. 3D conformations were generated using Merk Molecular Force Field 94[34] with 400 maximum number of conformers for each chemical structure. Shape and pharmacophore screening were performed with ROCS[35] based on lead molecules described in literature[36]. FRED program[31] was used to dock conformers generated with Omega to the GLUT5 model. Ranking of hits was done using a combo score with 20%, 60% and 20% weights given to ECFP, ROCS and FRED scores, respectively. A total of 347 top scoring hits were selected based on the combo score described above, out of which 175 chemicals (FIG. 9) were purchased and tested in GLUT5 proteoliposomes for inhibition of the fructose entrance counterflow transport.

Protein Expression and Purification of Wild-Type and Mutant GLUTs cDNAs of GLUT1, 3, 4 and 5 were purchased from Open Biosystems (GE Healthcare). cDNAs of GLUT2 was a gift from Prof. Graeme Bell at University of Chicago. Full length DNA was subcloned into pFastBac1 (Life Technologies) vector with a N-terminal hexahistidine tag. Bacmids were generated in DH10Bac *E. coli* cells (Life Technologies). Baculoviruses were produced using Cellfectin II Reagent and amplified in Sf21 insect cells (Life Technologies). Cells were maintained at 26° C., and P1 ($10^6$ pfu/mL) was collected from infected cells after 72 hours. SF21 cells were propagated in HyClone SFX-Insect media (GE Healthcare), supplemented with 5% fetal bovine serum (Biowest), 4.8 mM glutamine, antibiotics (100 units/mL Penicillin G and 100 μg/mL streptomycin sulfate) and amphotericin B (2.5 μg/mL). For recombinant protein expression, SF21 cells in suspension culture at 2×$10^6$ cells/ml were infected with P3 viral stock ($10^8$ pfu/mL), at an MOI of 1.0 pfu/cell. Four days after viral infection, cells from 1 L culture were collected by centrifugation at 2,000 g and 25°C. The cell pellet was resuspended in 120 mL of 50 mM sodium phosphate ($NaP_i$) (pH 7.5), 5% (v/v) glycerol, 200 mM sodium chloride (buffer A), with protease inhibitors (1 mM AEBSF, 10 μM E-64, 10 μM pepstatin A, 1 μM Aprotinin, 20 µM Bestatin, 20 µM Leupeptin), at 4° C., and disrupted by sonication (Branson Ultrasonic). n-Dodecyl-β-D-malto-pyranoside (DDM, EMD chemicals) was added to a final concentration of 1% (w/v) in the broken cell solution, and the mixture was incubated at 4° C. with stirring, for 4 hours. The solubilized protein solution was clarified by ultracentrifugation at 200,000 g and 4° C. for 1 hour, and the supernatant was loaded onto the Ni-NTA resin (Novagen) and washed with buffer containing 50 mM $NaP_i$ (pH 7.5), 500 mM NaCl, 5-20 mM imidazole, 5% (v/v) glycerol and 0.05% (w/v) DDM. GLUT1 (or GLUT2-5, wild-type or mutants) was eluted with buffer A, containing 300 mM imidazole and 0.05% DDM (w/v). To generate DNA for mutant proteins, site-directed mutagenesis was performed on the pFastBac1 plasmid constructs of wild-type proteins and verified by DNA sequencing[37]. Mutant proteins were expressed and purified in the same manner as wild-type proteins with no modifications.

Proteoliposome Purification

Proteoliposomes were generated according to the protocol of[16,38] with minor modifications. Liposomes were made from a 95%/5% mix of soy phosphatidylcholine and cholesterol (Avanti Polar Lipids). Prepared liposomes were destabilized with 4 mM Triton X-100 and mixed with purified protein in a 100:1 (w/w) ratio in 100 mM $KP_i$ (pH 7.5), 20% (v/v) glycerol, 200 mM glucose for GLUT1-4 and $GLUT1_{F379H}$ or fructose for GLUT5 (wild-type and H387F mutant) and GLUT2. Detergent was removed by several additions of SM2 BioBeads (BioRad) and incubated overnight at 4° C. After filtering out BioBeads, proteoliposomes were diluted with 100 mM $KP_i$ (pH 7.5), 200 mM glucose for GLUT1 (wild-type and F379H mutant) and GLUT2-4 or fructose for GLUT5 (wild-type and H387F mutant) and GLUT2, and then collected by ultracentrifugation at 200,000 g, for 1 h, at 4° C. Proteoliposomes were resuspended in 100 mM $KP_i$ (pH 7.5), to an $OD_{600\ nm}$ ~30.

Entrance Counter-Flow Transport Assay for Human GLUTs

For the entrance counterflow transport in proteoliposomes, the assay was started by the addition of 5 µL proteoliposomes solution ($OD_{600\ nm}$ ~30) to 200 µL, assay solution, containing 10 µM $^{14}C$-radiolabeled glucose (for GLUT1 wild-type or F379H mutant and GLUT2-4) or fructose (for GLUT5 wild-type or H387F mutant and GLUT2) (Moravek Biochemicals) in 100 mM KPi buffer at pH 7.5. After one minute (or different specified time points when the time-dependent counter-flow transport activity was measured), the transport was stopped with ice-chilled quench buffer [0.1 M KPi (pH 5.5) and 0.1 M lithium chloride]. The solution was filtered with a cellulose nitrate membrane filter (Whatman; 0.4 µm pore size), and the filter was washed three times with quench buffer. The membrane filter was placed into a vial filled with BioSafe II scintillation liquid (Research Products International Corp.), and radioactivity was quantified with LS 6500 scintillation counter (Beckman). Compounds tested for the inhibition study were purchased from Sigma Chemicals (FIG. 9). Stocks of 100 mg/ml for each compound were made in either water or dimethyl sulfoxide (DMSO). Chemicals at 1 mM final concentration in the assay volume were screened for inhibition of GLUT5 fructose transport in proteoliposomes. Tested inhibitors were added 1 min prior to addition of proteoliposomes solution. Cytochalasin B (Enzo Life Sciences) and phloretin (Alfa Aesar) were dissolved in DMSO at stock concentrations of 100 mM. Kinetic parameters were determined by nonlinear algorithm plots supplied by Prism (GraphPad Software). DMSO up to 5% concentration in the transport assay did not affect activity. Data is presented as relative activity normalized to radioactivity of no inhibitor added as 100% and empty liposomes as 0%.

Transport Assay for $GlcP_{Se}$

Glucose transport assay for $GlcP_{Se}$, wild-type and F348H mutant, was performed as described previously[16]. $GlcP_{Se}$ was cloned into the pBAD vector (Invitrogen) with C-terminal 6×His tag. F348H mutation was done with the site-directed mutagenesis method[37]. $GlcP_{Se}$ proteins were expressed in the glucose transporter deficient *Escherichia coli* strain JM1100. Cells were grown at 37° C., in Luria Broth medium, with 100 µg/mL ampicillin. Protein expression was induced with 0.3 mM L-arabinose at $O.D._{600\ nm}$ 0.6. After 3 hours, cells were harvested by centrifugation at 2,500 g for 5 min. The right-side-out (RSO) membrane vesicles of JM1100 *E. coli* cells were prepared as described previously[16,39,40]. Transport assay was initiated by the addition of $^{14}C$-radiolabeled glucose (Moravek Biochemicals) to 50 µL RSO vesicles in 100 mM KPi buffer pH 7.5, at $O.D._{600\ nm}$ of 2.0. After one minute, the transport was stopped and the radioactivity was measured as described below. When inhibitors were used, they were incubated with RSO vesicles 1 minute before transport initiation.

Results

Generation of Virtual Database of Potential GLUT5 Inhibitors

The structure of GLUT5 was initially generated on the basis of $GlcP_{Se}$ crystal structure (PDB ID 4LDS), with Coot[17]. From Chemnavigator's (http://www.chemnavigator.com) database of 6,273,384 small molecular compounds, a list of 374 possible GLUT5 ligands was created with virtual screening. Among these, considering commercial availability and cost, 175 were purchased and tested for inhibition of GLUT5 transport activity (FIG. 9 for a complete list of the tested compounds). After the virtual screening studies, the crystal structure of GLUT1 was published and we generated a new GLUT5 model on the basis of GLUT1 (PDB ID 4PYP). The two GLUT5 models were very similar, consistent with the similarity of the crystal structures of $GlcP_{Se}$ and GLUT1; the root-mean-square deviations for the crystal structures superposition in the transmembrane helices was less than 1.5 Å (calculated with Superpose[18]).

Screening for Inhibitors of GLUT5

Figure 3:
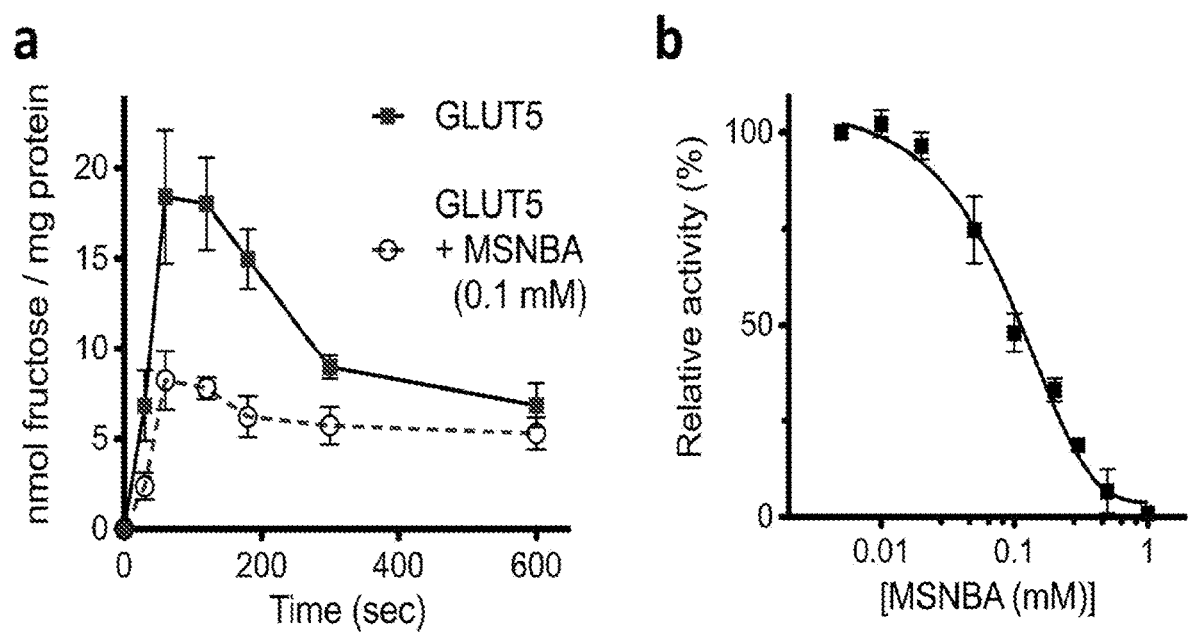
FIG. 3 shows shows MSNBA inhibition of GLUT5. (a) Fructose entrance counter-flow transport in GLUT5 proteoliposomes, in the absence and presence of 0.1 mM MSNBA. Transport was initiated by the addition of GLUT5 proteoliposomes to reaction solution containing 10 μM $C^{14}$-fructose, with or without 0.1 mM MSNBA, and stopped at the indicated time points. Error bars represent standard deviation from 3 different measurements. (b) Dose-dependent MSNBA inhibition of GLUT5 fructose transport in proteoliposomes. Each point was measured a minute after transport initiation, using the entrance counter-flow transport assay. $IC_{50}$ of MSNBA inhibition was 0.10±0.03 mM. Curve was generated with Prism (GraphPad Software).

Human GLUT5 was recombinantly expressed in insect cells, purified by immobilized metal ion affinity chromatography, and reconstituted in artificial lipids. The fructose entrance counterflow assay with GLUT5 proteoliposomes was constant between 1 and 2 minutes, so the inhibition of transport by compounds was assessed one minute after assay initiation (FIG. 3a). The 175 potential GLUT5 ligands were grouped in batches of 5 chemicals (each at 1 mM concentration) and tested for inhibition of the fructose transport by GLUT5, in proteoliposomes, with the entrance counter-flow transport assay.

For batches that caused decreased fructose transport, the individual compounds from the group were tested for inhibition. We found one chemical with inhibitory activity against GLUT5: 4-(methylsulfonyl)-2-nitrophenyl]-1,3-benzodioxol-5-amine (MSNBA) (The chemical structure of MSNBA is shown above and in FIG. 4b). The entrance counter-flow fructose transport by GLUT5 in proteoliposomes in the presence of 0.1 mM MSNBA is shown in FIG. 5a. The relative fructose transport by GLUT5 at different concentrations of MSNBA is shown in FIG. 3b; the non-linear curve fitted to an $IC_{50}$ of 0.10±0.03 mM, which is 100-fold lower than reported fructose $K_M$ values for GLUT5 (~10 mM)[12].

Determination of MSNBA Binding Site in GLUT5 Model

The docked MSNBA binding site in GLUT5 model is near the active site (FIG. 4a). MSNBA putatively interacts with residues S143, T171, Q288, Q289, N294, Y297, and H387 (FIG. 4b and FIG. 6), which vary in their degree of conservation, compared to residues of other GLUT members or GlcP$_{Se}$ (FIG. 2c). Q288, Q289 and N294 are strictly conserved and their mutations abolish transport activity in GLUT1[19] or GlcP$_{Se}$[16]. S143 and T171 are partially conserved in homologues that transport glucose. Y297 is a Phe in GLUT1-4 or Ile in GlcP$_{Se}$, while H387 is Phe in GLUT1-4 and GlcP$_{Se}$ (FIG. 2c). GLUT1, GLUT3, GLUT4 and GlcP$_{Se}$ transport glucose but not fructose, GLUT2 transports both fructose and glucose, while GLUT5 transports only fructose[6].

Figure 7:
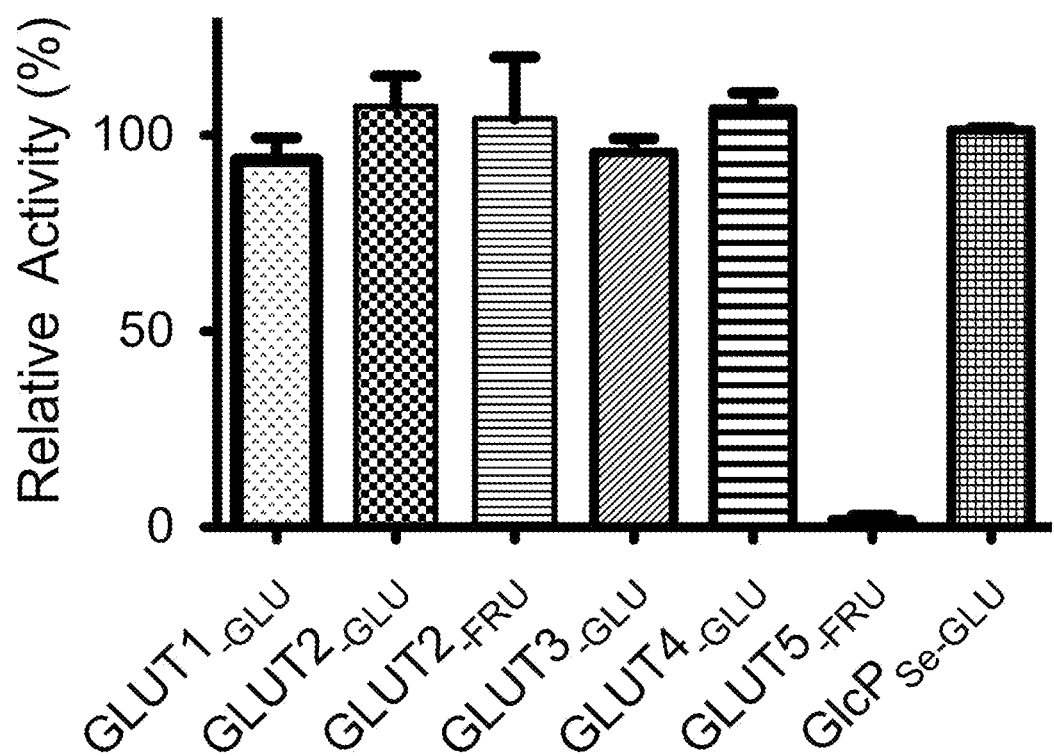
FIG. 7 shows the effect of 2 mM MSNBA on the relative transport activity of GLUT1-5 and $GlcP_{Se}$. Glucose (GLU) or fructose (FRU) transport activity was determined by the entrance counter-flow transport assay method in proteoliposomes. The measurements were done one minute after transport initiation. Error bars represent standard deviations from three different experiments.
Figure 8:
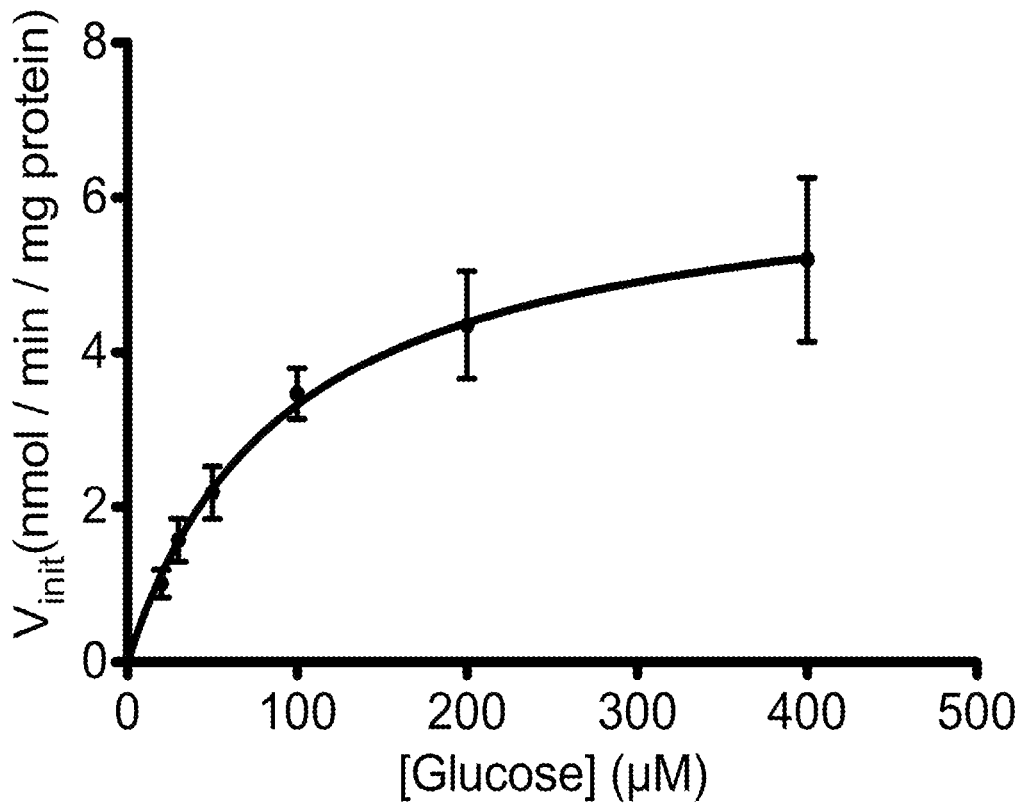
FIG. 8 shows the Michaelis-Menten plots for glucose uptake by $GlcP_{Se,F348H}$, in RSO vesicles. The experiments were conducted in JM1100 $E.\ coli$ cells expressing $GlcP_{Se-F348H}$. Assay was performed at different glucose concentrations and stopped one minute after addition of $C^{14}$-glucose. Transport kinetic parameters were determined with Prism: $K_M$=94±19 μM, $V_{max}$=6.4±0.5 nmol/min/mg. Error bar is standard deviation from 3 different measurements.

Given the partial conservation of the MSNBA binding site in other GLUTs and GlcP$_{Se}$, we checked whether MSNBA inhibits GLUT1-4 or GlcP$_{Se}$. Glucose transport of GLUT1, GLUT2, GLUT3 and GLUT4 and fructose transport of GLUT2 were assayed by the entrance counter-flow method in proteoliposomes constructed with the respective recombinant human GLUT produced in insect cells. Glucose transport of GlcP$_{Se}$ was measured in right-side-out (RSO) vesicles of JM1100 E. coli cells (that lack endogenous glucose transport) expressing GlcP$_{Se}$. Consistent with previous reports[4,6,16,20,21], the activities of GLUT5, GLUT1 and GlcP$_{Se}$ were affected by known GLUT1 inhibitors (FIG. 3a-c): phloretin, and cytochalasin B inhibited GLUT1 and GlcP$_{Se}$, but not GLUT5. High concentrations of MSNBA (2 mM) did not influence the glucose transport of GLUT1, GLUT2, GLUT3, GLUT4 or GlcP$_{Se}$ (FIG. 5b, 5c and FIG. 7) or the fructose transport of GLUT2 (FIG. 7), but completely abolished GLUT5 fructose transport (FIG. 5a).

As MSNBA seemed to be specific for GLUT5, we focused on the residues in the MSNBA predicted binding site that were different from GLUT5 compared to GLUT1-4 and GlcP$_{Se}$. Among these, H387 of GLUT5 potentially interacts with the nitroxide group of MSNBA (FIG. 4b and FIG. 6), but is a Phe in GLUT1-4 as well as GlcP$_{Se}$ (FIG. 4c). To test if this residue is important for MSNBA inhibition, we constructed and expressed three mutant proteins: GlcP$_{Se,F348H}$, GLUT1$_{F379H}$, and GLUT5$_{H387F}$. As with the wild-type proteins, GLUT1$_{F379H}$ and GLUT5$_{H387F}$ were recombinantly produced in insect cells, purified and reconstituted in proteoliposomes. Their transport activity was assayed by the entrance counter-flow method in proteolipsomes. Glucose transport of GlcP$_{Se,F348H}$ was determined in JM1100 E. coli cells in right-side-out (RSO) vesicles. Unlike in wild-type transporters, 2 mM MSNBA inhibited 75% of the transport activity of GlcP$_{Se,F348H}$ (FIG. 3f), and left GLUT5$_{H387F}$ largely unaffected (FIG. 5d). GLUT1$_{F379H}$ remained insensitive to MSNBA, but had altered response to cytochalasin B and phloretin (FIG. 5e), compared to wild-type (FIG. 5b); at 2 mM concentration phloretin no longer inhibited glucose transport, whilst cytochalasin B inhibited only ~37% of GLUT1$_{F379H}$ glucose transport.

Discussion

Various diseases are associated with changes in GLUT5 activity and regulation patterns. Disruption of normal GLUT5 function can be a cause or side effect of pathologies like diabetes, breast cancer, hypertension and others[7]. Inhibition of GLUT5 in cancers associated with drastic overexpression of GLUT5 can be used to deprive tumor cells of energy. Unlike GLUT1, which is widely distributed in various tissues, GLUT5's tissue expression is mostly restricted to the small intestine[22], in healthy humans. Therefore, GLUT5 is a viable therapeutic target provided that specific effectors of its function are found, particularly ones that do not impact GLUT1 activity.

To determine ligands for GLUT5 we used a convergent virtual and in vitro screening approach, one that previously allowed us to identify several "first-in-class" bioactive molecules: small molecule antagonists for the formyl peptide receptors[23]; the first agonist for the G-protein estrogen receptor (GPER, or GPR30), "G1"[24], and the first antagonist, "G15"[25]; a selective ABCG2 transporter inhibitor[26]; and two HIV integrase inhibitors, Raltegravir and Elvitegravir, that block metnase, a DNA-repair enzyme[27].

Our virtual screening procedure follows a previously described workflow[28], which centers on chemical structure standardization and preparation, followed by careful evaluation of the binding site. In this work, we virtually screened a chemical library of over 6 million compounds against a putative binding site model of GLUT5, and reduced the number of possible ligands to 374. Among these, we identified 175 commercially affordable chemicals which were tested for inhibition of GLUT5 activity in vitro.

Figure 5:
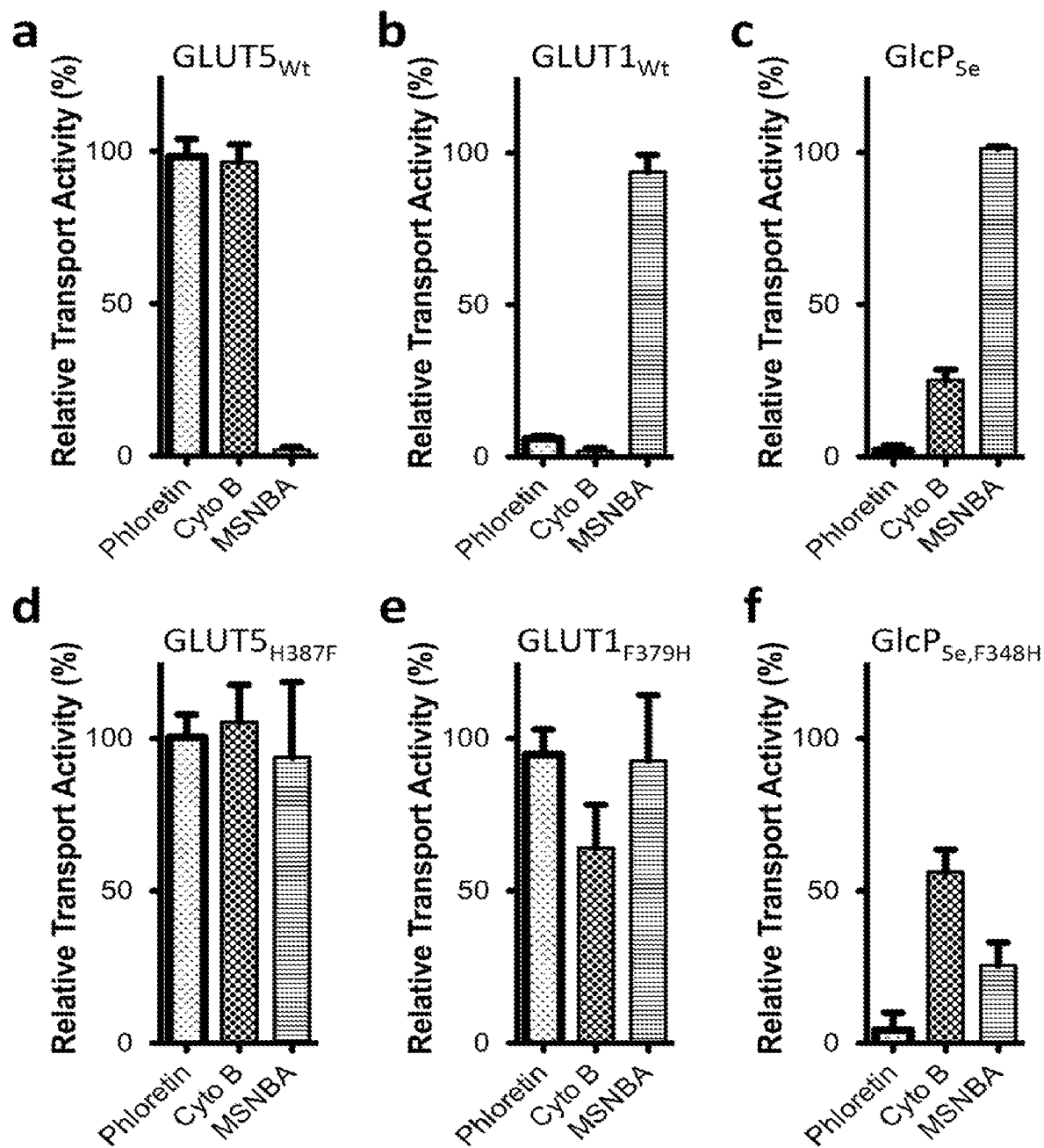
FIG. 5 shows the effect of MSNBA and common GLUT1 inhibitors on the relative transport activity of wild-type and mutants of GLUT5, GLUT1 and $GlcP_{Se}$. (a, b, d, e) Glucose (for GLUT1 wild-type and F379H mutant) or fructose (for GLUT5 wild-type and H387F mutant) entrance counter-flow transport was measured one minute after initiation of transport with 10 μM $C^{14}$-hexose (glucose for GLUT1 transporters, fructose for GLUT5 transporters), in the presence of 2 mM phloretin, cytochalasin B or MSNBA. Error bars represent standard deviations from 3 different experiments. (c, f) Glucose uptake for $GlcP_{Se}$ was measured one minute after initiation of transport with $C^{14}$-glucose at $K_M$ concentration (30 μM for wild-type[16], 90 μM for mutant, see FIG. 8) in the presence of 2 mM phloretin, cytochalasin B or MSNBA, in right-side-out vesicles. Error bars represent standard deviations from 3 different experiments.

Consistent with previous reports, known GLUT1 inhibitors such as cytochalasin B and phloretin did not alter the transport activity of GLUT5 (FIG. 3a). Among tested compounds, we found that MSNBA is an inhibitor of human GLUT5, with an IC$_{50}$ of 0.10±0.03 mM (FIG. 5). Furthermore, this inhibitor did not affect the transport of human GLUT1-4 or GlcP$_{Se}$ (FIG. 5b, 5c and FIG. 7), suggesting that MSNBA is specific for GLUT5. As successful drug candidates against GLUT5 need to be specific for this transporter, compared to GLUT members that transport glucose, binding of MSNBA to GLUT5 offered the opportunity to examine the molecular basis of ligand specificity in GLUT5.

Figure 6:
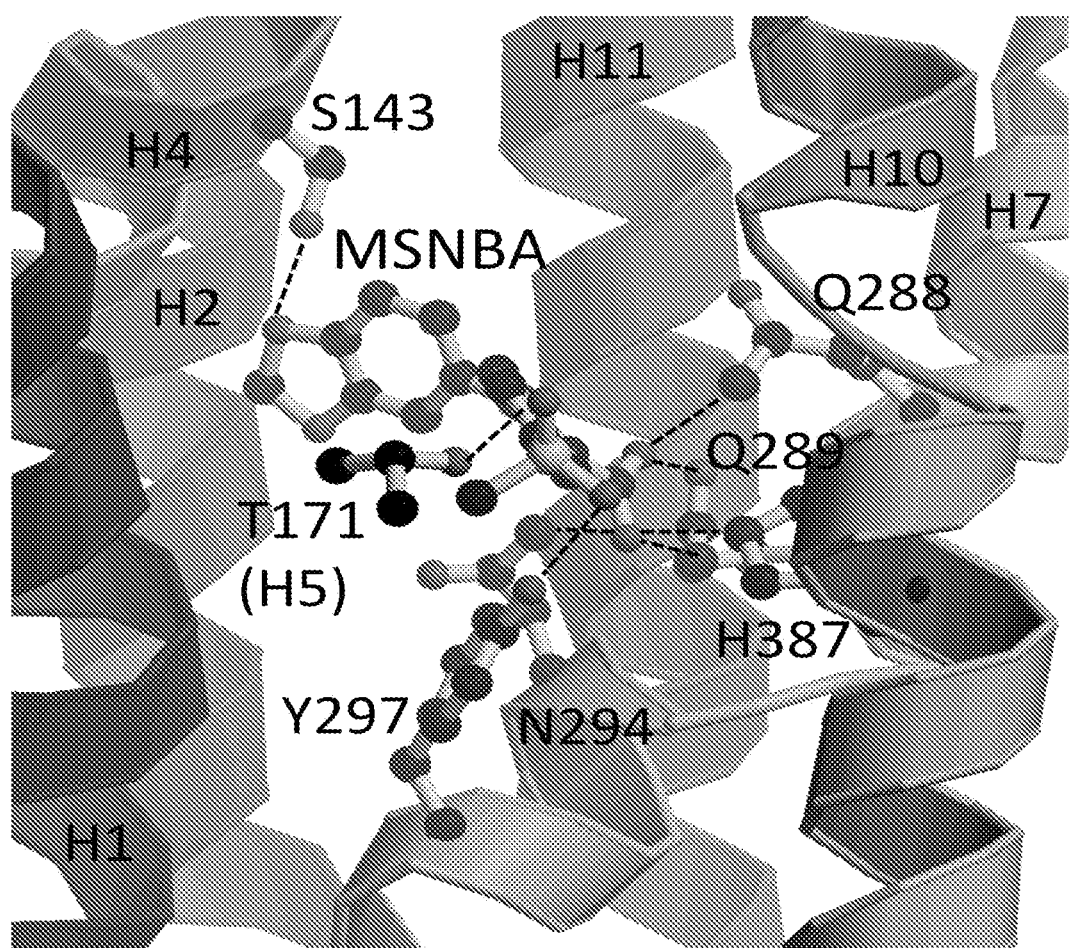
FIG. 6 shows a close-up of interactions between MSNBA and side chains of GLUT5. Interacting residues come from helices 4 (S143), 5 (T171), 7 (Q288, Q289, N294 and Y297), and 10 (H387). Helix 5 was omitted for clarity. This figure was drawn with Molscript[40] and raster3D[41].

Docking MSNBA into the GLUT5 model predicted that the inhibitor binds near the active site, within interacting distance from partially-conserved residues in GLUT family, specifically S143, T171, Q288, Q289, N294, Y297, and H387 (FIG. 4). The fact that MSNBA did not affect the activity of GLUT1-4 or GlcP$_{Se}$ (FIG. 5b, 5c and FIG. 7) can be interpreted as indicating a non-essential role for residues conserved among GLUT1, GLUT5 and GlcP$_{Se}$ of the putative MSNBA binding site. Among the variable residues of the MSNBA binding pocket, H387 might interact with the nitroxide group of MSNBA (FIG. 4b and FIG. 6). This residue is replaced by a Phe in glucose transporters, including GLUT1-4 and the bacterial GlcP$_{Se}$ (FIG. 4c). Therefore, we constructed mutants in GLUT1, GLUT5 and GlcP$_{Se}$ in which we interchanged His and Phe, to probe the role of H387 in MSNBA inhibition and ligand selectivity.

Compared to wild-type transporters (FIG. 5a-c), at high concentration of MSNBA (2 mM), GLUT5$_{H387F}$ was almost unsusceptible to MSNBA inhibition, retaining 93% of its activity (FIG. 5d), GlcP$_{Se,F348H}$ became sensitive to the inhibitor, with 75% of its activity abolished (FIG. 5f), while GLUT1$_{F378H}$ remained unaffected by MSNBA (FIG. 5e). These data confirm that H387 of GLUT5 is important for the interaction with MSNBA, though not sufficient on its own, since GLUT1$_{F379H}$ was not inhibited by MSNBA.

Interestingly, though, the susceptibility of GLUT1$_{F379H}$ mutant to well-known GLUT1 inhibitors like cytochalasin B and phloretin (FIG. 5e) was remarkably different from that of the wild-type GLUT1 (FIG. 5b). Thus, phloretin ceased to inhibit glucose transport activity of GLUT1$_{F379H}$ while cytochalasin B was significantly less potent, compared to wild-type GLUT1. On the other hand, while the decreased cytochalasin B inhibition of GlcP$_{Se,F348H}$ mimicked the response of GLUT 1$_{F379H}$ to this inhibitor, phloretin still inhibited GlcP$_{Se,F348H}$ (FIG. 5f). Previous studies indicated that cytochalasin B binds on the cytosolic side of GLUT1[29], so it is intriguing that a mutation close to the active site alters cytochalasin B inhibition. It is believed that cytochalasin B binding to GLUT1 locks the transporter, preventing the cycling between the inward- and outward-facing conformations necessary for substrate transport from one side of the membrane to the other. Thus, the F379H mutation in GLUT1 may destabilize cytochalasin B bound conformation of GLUT1. Unlike cytochalasin B, phloretin might bind in the proximity of the active site[30]. Therefore the insensitivity of GLUT1$_{F379H}$ to phloretin may be due to a direct effect on phloretin binding by this mutation. It is unclear, though, why the same mutation in GlcP$_{Se}$ does not abolish phloretin inhibition in this transporter as well or why GLUT1$_{F379H}$ remained insensitive to MSNBA. GlcP$_{Se}$ has a K$_M$ for glucose ~100-fold lower than GLUT1. Also, unlike GLUT1, GlcP$_{Se}$ is specific for glucose; it does not transport galactose. So, even though both GLUT1 and GlcP$_{Se}$ transport glucose, there are differences in their substrate transport (affinity and specificity), which are translated also in inhibitor interactions. It is possible for GLUT1$_{F379H}$ to be affected by MSNBA, but at much higher concentrations than 2 mM (which run into solubility limit for the compound). Phloretin, on the other hand, seems to hit on an active site difference between GLUT1 and GlcP$_{Se}$, which will need to be defined by future mutational and structural studies.

The bioactivity profile of MSNBA was evaluated using three different online resources: i) PubChem (https://pubchem.ncbi.nlm.nih.gov), which has an entry for MSNBA (CID 4783927), does not show recorded bioactivities for this compound; ii) ChEMBL (https://www.ebi.ac.uk/chembldb), and SureChEMBL (https://www.surechembl.org), do not have matching entries for this compound. The on-line chemical portal, ChemSpider (https://www.chemspider.com), does not have additional information compared to PubChem. These searches indicate that there is no patented or published bioactivity profile for MSNBA, which further confirms our observations that this compound is highly specific, and therefore may serve as the first-in-class chemical probe for GLUT5.

Taken together the data presented here converge to suggest that, despite the overall similarity of GLUT members, small differences in their active site can significantly impact ligand selectivity. MSNBA inhibits GLUT5 by binding at the active site and, although it is not a fructose analog, it appears to be selective for GLUT5 and is not recognized by GLUT1, GLUT2, GLUT3 and GLUT4. While GLUT2 also transports fructose, it also transports glucose, and its activity is not perturbed by MSNBA, suggesting that MSNBA mimics GLUT5 substrate specificity. Thus, while the molecular determinants of substrate specificity in GLUT1 and GLUT5 remain unclear, small molecules of therapeutic interest that could selectively modulate these transporters might be within reach. H387 in GLUT5 is an important residue for ligand selectivity, and its contribution could perhaps be exploited when designing GLUT5 specific ligands. MSNBA may be an important starting point in the rational design of novel therapeutic approaches against obesity, diabetes and cancer, as the first chemical probe for GLUT5.

REFERENCES

1. Vos, M. B., Kimmons, J. E., Gillespie, C., Welsh, J. & Blanck, H. M. Dietary fructose consumption among US children and adults: the Third National Health and Nutrition Examination Survey. *Medscape J. Med* 10, 160 (2008).
2. Tappy, L. & Lê, K.-A. Metabolic effects of fructose and the worldwide increase in obesity. *Physiol. Rev.* 90, 23-46 (2010).
3. Hwang, I. S., Ho, H., Hoffman, B. B. & Reaven, G. M. Fructose-induced insulin resistance and hypertension in rats. *Hypertension* 10, 512-516 (1987).
4. Burant, C. F., Takeda, J., Brot-Laroche, E., Bell, G. I. & Davidson, N. O. Fructose transporter in human spermatozoa and small intestine is GLUT5. *J. Biol. Chem.* 267, 14523-14526 (1992).
5. Thorens, B. & Mueckler, M. Glucose transporters in the 21st Century. *Am. J. Physiol. Endocrinol. Metab.* 298, E141-145 (2010).
6. Uldry, M. & Thorens, B. The SLC2 family of facilitated hexose and polyol transporters. *Pflüg. Arch. Eur. J. Physiol.* 447, 480-489 (2004).
7. Douard, V. & Ferraris, R. P. Regulation of the fructose transporter GLUT5 in health and disease. *Am. J. Physiol.—Endocrinol. Metab.* 295, E227-E237 (2008).
8. David, E. S., Cingari, D. S. & Ferraris, R. P. Dietary Induction of Intestinal Fructose Absorption in Weaning Rats. *Pediatr. Res.* 37, 777-782 (1995).
9. Stuart, C. A., Howell, M. E. A. & Yin, D. Overexpression of GLUT5 in Diabetic Muscle Is Reversed by Pioglitazone. *Diabetes Care* 30, 925-931 (2007).
10. Mate, A., Barfull, A., Hermosa, Á. M., Planas, J. M. & Vázquez, C. M. Regulation of D-Fructose Transporter GLUT5 in the Ileum of Spontaneously Hypertensive Rats. *J. Membr. Biol.* 199, 173-179 (2004).
11. Godoy, A. et al. Differential subcellular distribution of glucose transporters GLUT1-6 and GLUT9 in human cancer: Ultrastructural localization of GLUT1 and GLUT5 in breast tumor tissues. *J. Cell. Physiol.* 207, 614-627 (2006).
12. Zamora-León, S. P. et al. Expression of the fructose transporter GLUT5 in human breast cancer. *Proc. Natl. Acad. Sci. U.S.A.* 93, 1847-1852 (1996).
13. Gaster, M., Staehr, P., Beck-Nielsen, H., Schrøder, H. D. & Handberg, A. GLUT4 Is Reduced in Slow Muscle Fibers of Type 2 Diabetic Patients Is Insulin Resistance in Type 2 Diabetes a Slow, Type 1 Fiber Disease? *Diabetes* 50, 1324-1329 (2001).
14. Deng, D. et al. Crystal structure of the human glucose transporter GLUT1. *Nature* 510, 121-125 (2014).
15. Sun, L. et al. Crystal structure of a bacterial homologue of glucose transporters GLUT1-4. *Nature* 490, 361-366 (2012).
16. Iancu, C. V., Zamoon, J., Woo, S., Aleshin, A. & Choe, J. Crystal structure of a glucose/H+ symporter and its mechanism of action. *Proc. Natl. Acad. Sci. U.S.A.* 110, 17862-17867 (2013).
17. Emsley, P., Lohkamp, B., Scott, W. G. & Cowtan, K. Features and development of Coot. *Acta Crystallogr. D Biol. Crystallogr.* 66, 486-501 (2010).
18. Krissinel, E. & Henrick, K. Secondary-structure matching (SSM), a new tool for fast protein structure alignment in three dimensions. *Acta Crystallogr. D Biol. Crystallogr.* 60, 2256-2268 (2004).
19. Hruz, P. W. & Mueckler, M. M. Cysteine-scanning mutagenesis of transmembrane segment 7 of the GLUT1 glucose transporter. *J. Biol. Chem.* 274, 36176-36180 (1999).

20. Corpe, C. P. et al. The regulation of GLUT5 and GLUT2 activity in the adaptation of intestinal brush-border fructose transport in diabetes. *Pflüg. Arch. Eur. J. Physiol.* 432, 192-201 (1996).
21. Kasahara, T. & Kasahara, M. Expression of the rat GLUT1 glucose transporter in the yeast *Saccharomyces cerevisiae*. *Biochem. J.* 315 (Pt 1), 177-182 (1996).
22. Davidson, N. O. et al. Human intestinal glucose transporter expression and localization of GLUT5. *Am. J. Physiol.* 262, C795-800 (1992).
23. Young, S. M. et al. Duplex high-throughput flow cytometry screen identifies two novel formylpeptide receptor family probes. *Cytom. Part J. Int. Soc. Anal. Cytol.* 75, 253-263 (2009).
24. Bologa, C. G. et al. Virtual and biomolecular screening converge on a selective agonist for GPR30. *Nat. Chem. Biol.* 2, 207-212 (2006).
25. Dennis, M. K. et al. In vivo effects of a GPR30 antagonist. *Nat. Chem. Biol.* 5, 421-427 (2009).
26. Strouse, J. J. et al. A selective ATP-binding cassette subfamily G member 2 efflux inhibitor revealed via high-throughput flow cytometry. *J. Biomol. Screen.* 18, 26-38 (2013).
27. Williamson, E. A. et al. Targeting the transposase domain of the DNA repair component Metnase to enhance chemotherapy. *Cancer Res.* 72, 6200-6208 (2012).
28. Bologa, C. G. & Oprea, T. I. Compound collection preparation for virtual screening. *Methods Mol. Biol. Clifton N.J.* 910, 125-143 (2012).
29. Mueckler, M. & Makepeace, C. Ligand-induced movements of inner transmembrane helices of Glut1 revealed by chemical cross-linking of di-cysteine mutants. *PloS One* 7, e31412 (2012).
30. Salas-Burgos, A., Iserovich, P., Zuniga, F., Vera, J. C. & Fischbarg, J. Predicting the three-dimensional structure of the human facilitative glucose transporter glut1 by a novel evolutionary homology strategy: insights on the molecular mechanism of substrate migration, and binding sites for glucose and inhibitory molecules. *Biophys. J.* 87, 2990-2999 (2004).
31. McGann, M. FRED pose prediction and virtual screening accuracy. *J. Chem. Inf. Model.* 51, 578-596 (2011).
32. Rogers, D. & Hahn, M. Extended-Connectivity Fingerprints. *J. Chem. Inf. Model.* 50, 742-754 (2010).
33. Hawkins, P. C. D., Skillman, A. G., Warren, G. L., Ellingson, B. A. & Stahl, M. T. Conformer Generation with OMEGA: Algorithm and Validation Using High Quality Structures from the Protein Databank and Cambridge Structural Database. *J. Chem. Inf. Model.* 50, 572-584 (2010).
34. Halgren, T. A. Merck molecular force field. I. Basis, form, scope, parameterization, and performance of MMFF94. *J. Comput. Chem.* 17, 490-519 (1996).
35. Hawkins, P. C. D., Skillman, A. G. & Nicholls, A. Comparison of shape-matching and docking as virtual screening tools. *J. Med. Chem.* 50, 74-82 (2007).
36. McQuade, D. T., Plutschack, M. B. & Seeberger, P. H. Passive fructose transporters in disease: a molecular overview of their structural specificity. *Org. Biomol. Chem.* 11, 4909-4920 (2013).
37. Braman, J., Papworth, C. & Greener, A. Site-directed mutagenesis using double-stranded plasmid DNA templates. *Methods Mol. Biol. Clifton N.J.* 57, 31-44 (1996).
38. Geertsma, E. R., Nik Mahmood, N. a. B., Schuurman-Wolters, G. K. & Poolman, B. Membrane reconstitution of ABC transporters and assays of translocator function. *Nat. Protoc.* 3, 256-266 (2008).
39. Kaback, H. R. Bacterial membranes. *Methods Enzymol.* 22, 99-120 (1971).
40. Short, S. A., Kaback, H. R. & Kohn, L. D. Localization of D-lactate dehydrogenase in native and reconstituted *Escherichia coli* membrane vesicles. *J. Biol. Chem.* 250, 4291-4296 (1975).
41. Kraulis, P. J. MOLSCRIPT: a program to produce both detailed and schematic plots of protein structures. *J. Appl. Crystallogr.* 24, 946-950 (1991).
42. Merritt, E. A. & Bacon, D. J. Raster3D: photorealistic molecular graphics. *Methods Enzymol.* 277, 505-524 (1997).
43. Larkin, M. A. et al. Clustal W and Clustal X version 2.0. *Bioinforma. Oxf. Engl.* 23, 2947-2948 (2007).

The invention claimed is:

1. A method of therapeutically treating a disease state or condition which is mediated through GLUT5 in a patient in need, comprising administering to said patient a therapeutically effective amount of a composition comprising at least one compound according to the chemical structure;

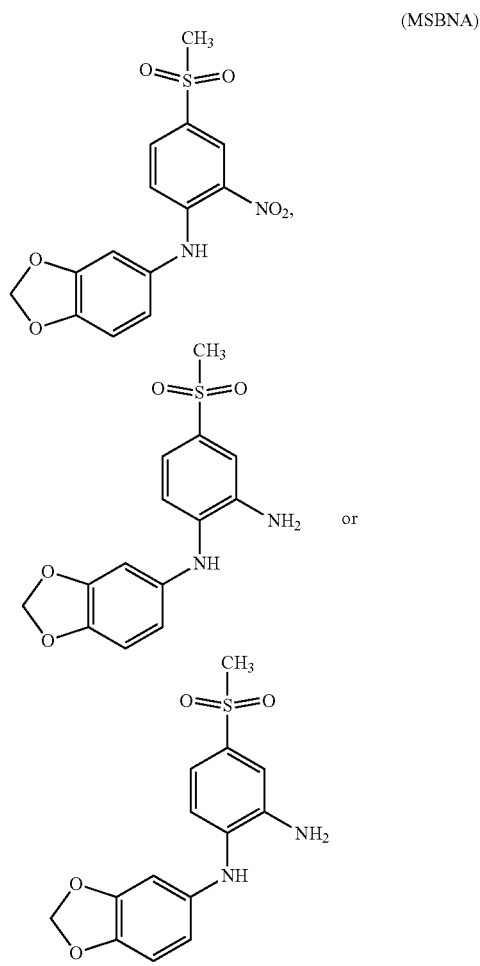

or a Pharmaceutically acceptable salt or solvate thereof, wherein said disease state or condition is diabetes type I, diabetes type II or a metabolic disease.

2. The method according to claim 1 wherein said metabolic disease is metabolic syndrome or fatty liver disease.

3. The method according, to claim 1 comprising administering to said patient an additional bioactive agent selected from the group consisting of an additional agent for the treatment of diabetes I or II or metabolic syndrome, a cardiovascular agent, a statin or a mixture thereof.

4. The method according to claim 3 wherein said additional bioactive agent is insulin, metformin, glipizide, glimepiride, glyburide, bromocriptine, pioglitazone, acarbose, sitagliptin, netaglinide, colesevelam, chlorpropamide, exenatide, liriglutide, repaglinide, rosiglitazone, saxagliptin, linaglipton, canagliflozin, miglitol, tolbutamide, tolazamide, mifepristone, dapagliflozin, pramlintide, alogliptin, albiglutide, empagliflozin, dulaglutide or a mixture thereof.

5. The method according to claim 3 wherein said additional bioactive agent is an agent for hypertensive emergency, an agent for pulmonary hypertension, an aldosterone receptor antagonist, an angiotensin converting enzyme inhibitor, an angiotensin receptor blocker, an antiadrenergic agent, an antianginal agent, an antiarrhythmic agent, an anticholinergic chronotropic agent, an ACE inhibitor, a calcium channel blocking agent, a thiazide, a beta blocker, a potassium sparing diuretic, a beta-adrenergic blocker, a catecholamine, a diuretic, an inotropic agent, a vasodilator, a renin inhibitor, a sclerosing agent, a vasopressin antagonist, a vasopressor or a mixture thereof.

6. The method according to claim 1 wherein said compound is

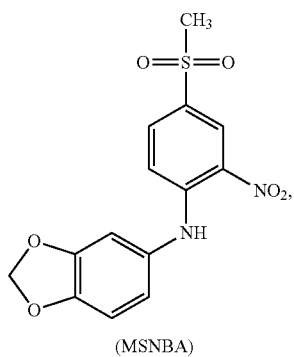 [SMILES: CS(=O)(=O)c1ccc(Nc2ccc3c(c2)OCO3)c([N+](=O)[O-])c1]

(MSNBA)

or a pharmaceutically acceptable salt thereof.

7. The method according to claim 2 wherein said compound is MSNBA or a pharmaceutically acceptable salt thereof.

8. The method according to claim 3 wherein said compound is MSNBA or a pharmaceutically acceptable salt thereof.

9. The method according to claim 4 wherein said compound is MSNBA or a pharmaceutically acceptable salt thereof.

10. The method according to claim 5 wherein said compound is MSNBA or a pharmaceutically acceptable salt thereof.

11. The method according to claim 1 wherein said disease state or condition is diabetes type I or II.

12. The method according to claim 1 wherein said disease state or condition is a metabolic disease.

13. A method of therapeutically treating a disease state or condition which is mediated through GLUT5 in a patient in need, comprising administering to said patient a therapeutically effective amount of a composition comprising a compound according to the chemical structure:

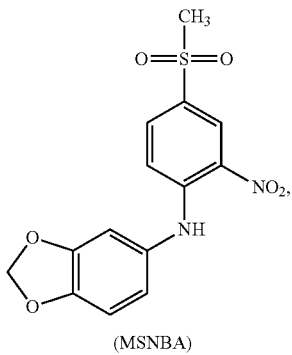 [SMILES: CS(=O)(=O)c1ccc(Nc2ccc3c(c2)OCO3)c([N+](=O)[O-])c1]

(MSNBA)

or a pharmaceutically acceptable salt thereof, wherein said disease state or condition is diabetes type I, diabetes type II, or a metabolic disease.

14. The method according to claim 13 wherein said disease state is diabetes type I or diabetes type II.

15. The method according to claim 13 wherein said disease state is a metabolic disease.

16. The method according to claim 15 wherein said metabolic disease is metabolic syndrome or fatty liver disease.

17. The method according to claim 16 wherein said fatty liver disease is non-alcohol fatty liver disease.

* * * * *